United States Patent
Qi et al.

(10) Patent No.: US 9,475,205 B2
(45) Date of Patent: Oct. 25, 2016

(54) METHOD OF MAKING A MECHANICAL FASTENER AND APPARATUS INCLUDING A ROLLER WITH PROTRUSIONS

(75) Inventors: Shengguang Qi, Zengcheng (CN); Xijun Mao, Shanghai (CN); Zhaobin Cheng, Guangzhou (CN); Thomas J. Gilbert, St. Paul, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 56 days.

(21) Appl. No.: 14/401,908

(22) PCT Filed: May 18, 2012

(86) PCT No.: PCT/CN2012/075734
§ 371 (c)(1),
(2), (4) Date: Jul. 23, 2015

(87) PCT Pub. No.: WO2013/170480
PCT Pub. Date: Nov. 21, 2013

(65) Prior Publication Data
US 2015/0360383 A1  Dec. 17, 2015

(51) Int. Cl.
*A61F 13/62* (2006.01)
*B32B 38/00* (2006.01)
(Continued)

(52) U.S. Cl.
CPC ........... *B26D 7/2621* (2013.01); *A61F 13/625* (2013.01); *A44B 18/0049* (2013.01); *A61F 13/622* (2013.01); *B29C 55/08* (2013.01);

(58) Field of Classification Search
CPC .................. B32B 2555/02; B32B 2038/0028; B29C 55/08; B29C 55/085; B29C 55/10–55/165; A61F 13/622; A61F 13/625; A61F 13/627; A44B 18/003–18/0019; A44B 18/0046–18/008

USPC ......................................................... 604/391
See application file for complete search history.

(56) References Cited

U.S. PATENT DOCUMENTS 3,252,181 A  5/1966  Hureau
3,616,154 A  10/1971 Dow et al.
(Continued)

FOREIGN PATENT DOCUMENTS

CN    102343671    2/2012
EP     0191355     8/1986
(Continued)

OTHER PUBLICATIONS

US 5,389,416, 02/1995, Mody et al. (withdrawn)
(Continued)

*Primary Examiner* — Carson Gross

(57) ABSTRACT

A method of making a mechanical fastener. The method includes providing a slit web having mechanical fastening elements and spreading the slit web in the cross-machine direction by directing the slit web over at least a first roller having first multiple protrusions around its peripheral surface. The slit web includes a plurality of interrupted slits that are interrupted by intact bridging regions of the web that divide the interrupted slits into a series of spaced slit portions aligned in the machine direction. The first multiple protrusions are positioned such that adjacent protrusions push through consecutive slit portions of a first of the interrupted slits to form a spread mechanical fastening web. An apparatus including the first roller and at least a subsequent roller is also disclosed.

16 Claims, 9 Drawing Sheets

(51) Int. Cl.
*B26D 7/26* (2006.01)
*B29C 55/08* (2006.01)
*A44B 18/00* (2006.01)

(52) U.S. Cl.
CPC ..... *B32B2038/0028* (2013.01); *Y10T 83/0448* (2015.04); *Y10T 83/783* (2015.04); *Y10T 156/1062* (2015.01)

(56) References Cited

U.S. PATENT DOCUMENTS

| | | | |
|---|---|---|---|
| 3,645,433 A | 2/1972 | Lucas et al. | |
| 3,724,737 A | 4/1973 | Bodnar | |
| 3,985,599 A | 10/1976 | Lepoutre et al. | |
| 3,985,600 A | 10/1976 | Blais | |
| 4,001,366 A | 1/1977 | Brumlik | |
| 4,152,479 A | 5/1979 | Larsen | |
| 4,176,775 A | 12/1979 | Brendemuehl | |
| 4,239,141 A | 12/1980 | Frye | |
| 4,288,884 A | 9/1981 | Bahls | |
| 4,294,240 A | 10/1981 | Thill | |
| 4,560,372 A | 12/1985 | Pieniak | |
| 4,676,784 A | 6/1987 | Erdman | |
| 4,775,310 A | 10/1988 | Fischer | |
| 4,842,794 A | 6/1989 | Hovis et al. | |
| 4,862,565 A | 9/1989 | Damour | |
| 4,925,080 A | 5/1990 | Crouse et al. | |
| 4,969,970 A | 11/1990 | Suzuki | |
| 5,043,036 A | 8/1991 | Swenson | |
| 5,077,870 A | 1/1992 | Melbye et al. | |
| 5,207,962 A | 5/1993 | Hovis et al. | |
| 5,232,533 A | 8/1993 | Tani et al. | |
| 5,256,231 A | 10/1993 | Gorman et al. | |
| 5,260,015 A | 11/1993 | Kennedy | |
| 5,290,377 A | 3/1994 | Aihara et al. | |
| 5,397,316 A | 3/1995 | LaVon | |
| 5,419,695 A | 5/1995 | Clegg | |
| 5,461,760 A | 10/1995 | Damour | |
| 5,476,437 A | 12/1995 | Damour | |
| 5,605,729 A | 2/1997 | Mody et al. | |
| 5,611,790 A | 3/1997 | Osborn, III | |
| 5,628,097 A | 5/1997 | Benson et al. | |
| 5,660,666 A | 8/1997 | Dilnik | |
| 5,692,271 A | 12/1997 | Provost | |
| 5,713,881 A | 2/1998 | Rezai | |
| 5,729,878 A | 3/1998 | Kurihara | |
| 5,776,343 A | 7/1998 | Cullen et al. | |
| 5,891,549 A | 4/1999 | Beretta | |
| 5,904,793 A | 5/1999 | Gorman | |
| 5,913,765 A | 6/1999 | Burgess et al. | |
| 5,953,797 A | 9/1999 | Provost et al. | |
| 6,093,870 A | 7/2000 | Carlsson | |
| 6,132,660 A | 10/2000 | Kampfer | |
| 6,146,369 A | 11/2000 | Hartman | |
| 6,190,594 B1 | 2/2001 | Gorman et al. | |
| 6,262,331 B1 | 7/2001 | Nakahata | |
| 6,287,665 B1 | 9/2001 | Hammer | |
| 6,391,420 B1 | 5/2002 | Cederblad | |
| 6,419,667 B1 | 7/2002 | Avalon | |
| 6,481,063 B2 | 11/2002 | Shepard | |
| 6,489,003 B1 | 12/2002 | Levitt | |
| 6,531,207 B1 | 3/2003 | Eaton | |
| 6,554,754 B2 | 4/2003 | VanRens | |
| 6,582,642 B1 | 6/2003 | Buzzell | |
| 6,627,133 B1 | 9/2003 | Tuma | |
| 6,835,256 B2 | 12/2004 | Menzies | |
| 6,843,762 B2 | 1/2005 | Munche et al. | |
| 6,984,412 B2 | 1/2006 | Tanaka | |
| 7,001,475 B2 | 2/2006 | Ausen | |
| 7,014,906 B2 | 3/2006 | Tuman | |
| 7,048,818 B2 | 5/2006 | Krantz | |
| 7,048,984 B2 | 5/2006 | Seth | |
| 7,125,400 B2 | 10/2006 | Igaue | |
| 7,198,743 B2 | 4/2007 | Tuma | |
| 7,214,334 B2 | 5/2007 | Jens et al. | |
| 7,219,403 B2 | 5/2007 | Miyamoto | |
| 7,223,314 B2 | 5/2007 | Provost | |
| 7,241,483 B2 | 7/2007 | Ausen | |
| 7,291,359 B2 | 11/2007 | Haskett et al. | |
| 7,371,302 B2 | 5/2008 | Miyamoto | |
| 7,407,496 B2 | 8/2008 | Petersen | |
| 7,622,180 B2 | 11/2009 | Seth | |
| 7,695,799 B2 | 4/2010 | Cree | |
| 7,855,316 B2 | 12/2010 | Meyer et al. | |
| 7,897,078 B2 | 3/2011 | Petersen | |
| 8,020,262 B2 | 9/2011 | Oertel | |
| 8,889,243 B2 | 11/2014 | Hanschen | |
| 9,138,031 B2 | 9/2015 | Wood | |
| 9,138,957 B2 | 9/2015 | Wood | |
| 9,155,669 B2 | 10/2015 | Petersen | |
| 2002/0112325 A1 | 8/2002 | Keohan | |
| 2003/0008106 A1 | 1/2003 | Guenther | |
| 2003/0130644 A1 | 7/2003 | Baker | |
| 2003/0229326 A1 | 12/2003 | Hovis et al. | |
| 2004/0000041 A1 | 1/2004 | Harashige | |
| 2004/0147890 A1 | 7/2004 | Nakahata et al. | |
| 2004/0261230 A1 | 12/2004 | Neeb | |
| 2004/0261232 A1 | 12/2004 | Kurtz, Jr. | |
| 2005/0123720 A1 | 6/2005 | Suzuki et al. | |
| 2006/0037691 A1 | 2/2006 | Haskett | |
| 2006/0107505 A1* | 5/2006 | Desai | A61F 13/512 26/51 |
| 2006/0288547 A1 | 12/2006 | Jackson | |
| 2007/0107571 A1 | 5/2007 | Saeki | |
| 2007/0134489 A1 | 6/2007 | Neugebauer | |
| 2009/0311465 A1 | 12/2009 | De Jong | |
| 2010/0100022 A1 | 4/2010 | Greener | |
| 2010/0179463 A1 | 7/2010 | Greener | |
| 2011/0147475 A1 | 6/2011 | Biegler et al. | |
| 2011/0151171 A1 | 6/2011 | Biegler et al. | |
| 2011/0151185 A1 | 6/2011 | Cree | |
| 2012/0011685 A1 | 1/2012 | Rocha | |
| 2012/0086145 A1 | 4/2012 | Nakamura | |
| 2012/0204383 A1* | 8/2012 | Wood | A44B 18/0046 24/306 |
| 2012/0330266 A1 | 12/2012 | Zonneveld et al. | |
| 2014/0142533 A1 | 5/2014 | Peltier | |
| 2014/0220328 A1 | 8/2014 | Ausen | |
| 2014/0234606 A1 | 8/2014 | Ausen | |
| 2014/0332999 A1 | 11/2014 | Rothwell | |
| 2014/0349062 A1 | 11/2014 | Chandrasekaran | |
| 2014/0349079 A1 | 11/2014 | Chandrasekaran | |
| 2015/0079337 A1 | 3/2015 | Ausen | |
| 2015/0096659 A1 | 4/2015 | Gilbert | |
| 2015/0096660 A1 | 4/2015 | Gilbert | |

FOREIGN PATENT DOCUMENTS

| | | |
|---|---|---|
| EP | 0755665 | 1/1997 |
| EP | 2277682 | 1/2011 |
| GB | 821959 | 10/1959 |
| GB | 914489 | 1/1960 |
| GB | 1055963 | 1/1967 |
| GB | 1075487 | 7/1967 |
| GB | 1275541 | 5/1972 |
| GB | 2017485 | 10/1979 |
| JP | 2010-29532 | 2/2010 |
| WO | WO 9402091 | 2/1994 |
| WO | WO 9610481 | 4/1996 |
| WO | WO 03-003961 | 1/2003 |
| WO | WO 2004-091437 | 10/2004 |
| WO | WO 2005-122818 | 12/2005 |
| WO | WO 2011-163020 | 12/2011 |
| WO | WO 2012-112768 | 8/2012 |
| WO | WO 2013-052371 | 4/2013 |
| WO | WO 2014-164242 | 10/2014 |

OTHER PUBLICATIONS

International Search report for PCT International Application No. PCT/CN2012/075734 mailed on Feb. 28, 2013, 6 pages.

* cited by examiner

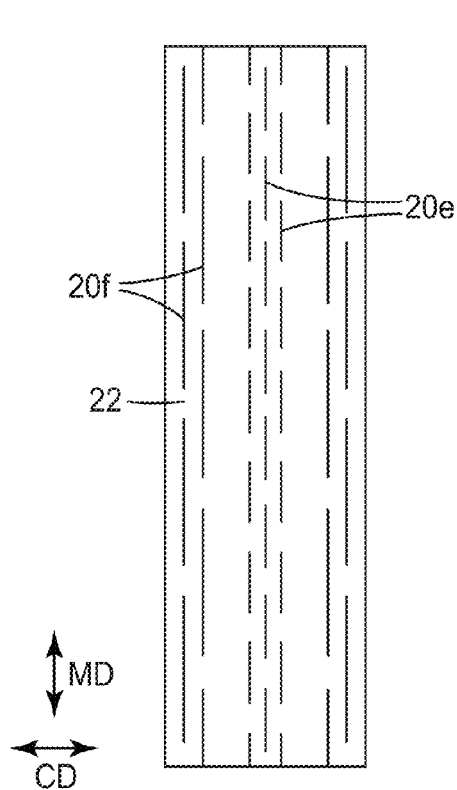
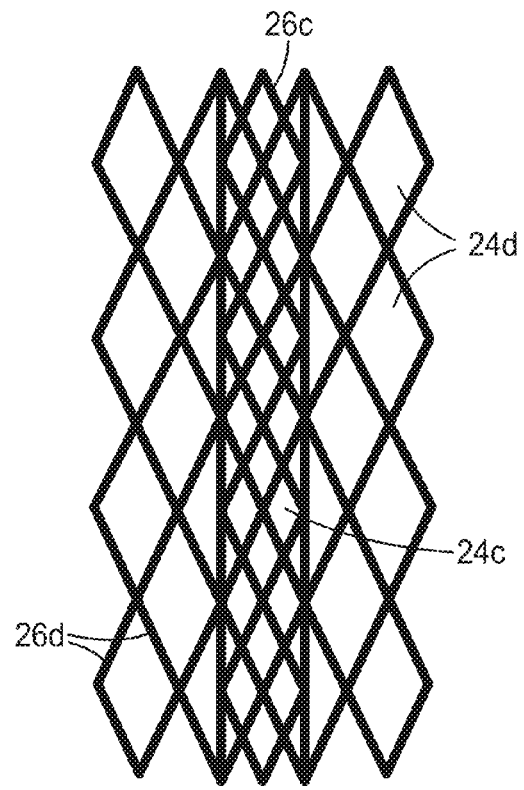
*Fig. 6A*  *Fig. 6B*
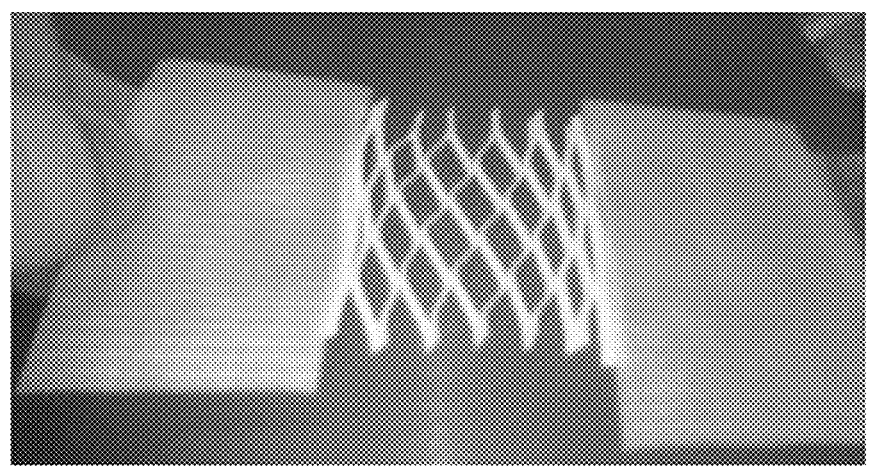
*Fig. 7*

METHOD OF MAKING A MECHANICAL FASTENER AND APPARATUS INCLUDING A ROLLER WITH PROTRUSIONS

BACKGROUND

Hook and loop fastening systems, where the hook member typically includes a plurality of closely spaced upstanding projections with loop-engaging heads, and the loop member typically includes a plurality of woven, nonwoven, or knitted loops, are useful for providing releasable attachment in numerous applications. For example, hook and loop fastening systems are widely used in wearable disposable absorbent articles to fasten such articles around the body of a person. In typical configurations, a hook strip or patch on a fastening tab attached to the rear waist portion of a diaper or incontinence garment, for example, can fasten to a landing zone of loop material on the front waist region, or the hook strip or patch can fasten to the backsheet (e.g., nonwoven backsheet) of the diaper or incontinence garment in the front waist region. Hook and loop fasteners are also useful for disposable articles such as sanitary napkins. A sanitary napkin typically includes a back sheet that is intended to be placed adjacent to the wearer's undergarment. The back sheet may comprise hook fastener elements to securely attach the sanitary napkin to the undergarment, which mechanically engages with the hook fastener elements.

Some hook members have been made with openings in the backing from which the hooks project. See, e.g., U.S. Pat. No. 4,001,366 (Brumlik) and U.S. Pat. No. 7,407,496 (Peterson) and Int. Pat. Appl. Pub. Nos. WO 2005/122818 (Ausen et al.) and WO 1994/02091 (Hamilton).

Some nonwoven materials have been made with openings. Such nonwovens have been attached to elastics or extensible pleated backings. See, e.g., U.S. Pat. Appl. Pub. No. 2004/0147890 (Nakahata et al.), Int. Pat. Appl. Pub. No. WO 1996/10481 (Abuto et al.), and European Patent No. EP 1066008 B1 (Eaton et al.).

SUMMARY

The present disclosure provides a method of making mechanical fastener using a web process. The mechanical fastener comprises openings made from multiple strands of a slit web having mechanical fastening elements with the strands attached to each other at bridging regions of the web and separated from each other between at least some of the bridging regions. The method includes using one or more rollers having multiple protrusions (e.g., ribs or pins) that spread apart strands of the slit web when the web is directed over the roller.

In one aspect, the present disclosure provides a method of making a mechanical fastener. The method includes providing a slit web having mechanical fastening elements and spreading the slit web in the cross-machine direction by directing the slit web over at least a first roller having first multiple protrusions around its peripheral surface. The slit web includes a plurality of laterally separated interrupted slits that are interrupted by intact bridging regions of the web that divide the interrupted slits into a series of spaced slit portions aligned in the machine direction. For at least some adjacent interrupted slits, the spaced slit portions are staggered in the cross-machine direction. The first multiple protrusions are positioned such that adjacent protrusions push through consecutive slit portions of a first one, two, or three of the interrupted slits to form a spread mechanical fastening web, which includes multiple strands of the slit web attached to each other at least at some of the intact bridging regions and separated from each other between at least some of the intact bridging regions. The first multiple protrusions may form a single row around the peripheral surface of the first roller to push through the consecutive slit portions of a first one of the interrupted slits, may be in the form of multiple pairs of protrusions forming two identical rows around the peripheral surface of the first roller to push through the consecutive slit portions of a first two of the interrupted slits, or may be in the form of a combination of these wherein the single row is centered between and offset from the multiple pairs of protrusions forming two identical rows to push through the consecutive slit portions of a first three of the interrupted slits.

In some embodiments, the method further includes directing the slit web over at least one second roller having multiple paired protrusions around its peripheral surface. The multiple paired protrusions are positioned such that adjacent pairs push through consecutive slit portions of second and third of the interrupted slits, which are on opposite sides of the first one, two, or three of the interrupted slits. In some embodiments, the method further includes directing the slit web over a series of second rollers, each having multiple paired protrusions around its peripheral surface. For each second roller, the multiple paired protrusions are positioned such that adjacent pairs push through consecutive slit portions of an opposing pair of the interrupted slits, which are on opposite sides of the first one, two, or three of the interrupted slits. For each consecutive roller in the series of second rollers, the paired protrusions and the opposing pair of the interrupted slits are spaced progressively further apart. In some embodiments, the method further includes directing the slit web over a series of third rollers, each having multiple groups of protrusions around its peripheral surface. For each third roller, the multiple groups of protrusions are positioned such that adjacent groups push through consecutive slit portions of a series of the interrupted slits. For each consecutive roller in the series of third rollers, the number of protrusions in each of the multiple groups of protrusions increases as the number of interrupted slits in the series of the interrupted slits increases.

In another aspect, the present disclosure provides an apparatus useful, for example, for spreading a slit web. The apparatus includes multiple rollers configured to handle a web in a continuous process. The multiple rollers include a first roller having first multiple protrusions around its peripheral surface and at least one subsequent roller having multiple sets of at least two protrusions around its peripheral surface. The first multiple protrusions may form a single row around the peripheral surface of the first roller, may be in the form of multiple pairs of protrusions forming two identical rows around the peripheral surface of the first roller, or may be in the form of a combination of these wherein the single row is centered between and offset from the multiple pairs of protrusions forming two identical rows. In some embodiments, the at least one subsequent roller is a second roller having multiple paired protrusions around its peripheral surface. In some embodiments, the at least one subsequent roller is included in a series of second rollers, each having multiple paired protrusions around its peripheral surface. For each consecutive roller in the series of second rollers, the paired protrusions are spaced progressively further apart. In some embodiments, the apparatus further includes a series of third rollers, each having multiple groups of protrusions around its peripheral surface, wherein for each consecutive roller in the series of third rollers, the number of protrusions in each of the multiple groups of protrusions increases.

The method allows openings to be provided in the mechanical fastener without wasteful material loss. The degree of spreading of the strands and the number of strands that are spread in the methods disclosed herein may be adjusted based upon, for example, the desired appearance, weight, or cost in the final product and may be controlled by specific design of the rollers having the protrusions.

The method disclosed herein may be useful, for example, for making a reticulated mechanical fastening web, laminate, strip, or patch that has a unique and attractive appearance. The openings can provide breathability and flexibility to the mechanical fastener, which may enhance the comfort of the wearer, for example, of an absorbent article comprising the mechanical fastener made by the method disclosed herein. The mechanical fastener also is typically able to cover a relatively large area with a relatively small amount of material, which may lower its cost. Also, because of the large area that may be covered by the mechanical fastener in an absorbent article, the mechanical fastener may provide performance enhancement, for example, by resist shifting forces such as torsional or rotational forces caused by movement of the wearer of the absorbent article. For example, in use, fitting an absorbent article such as a diaper about the wearer usually requires the front and back waist portions of the diaper to overlap each other. As the diaper is worn the movements of the wearer tend to cause the overlapping front and back waist portions to shift position relative to each other. Unless such shifting is limited, the fit and containment characteristics of the diaper may be degraded as the diaper is worn. The mechanical fastener made according to the present disclosure may provide improved fit and closure stability by resisting such shifting because of its relatively larger area and flexibility.

In this application, terms such as "a", "an" and "the" are not intended to refer to only a singular entity, but include the general class of which a specific example may be used for illustration. The terms "a", "an", and "the" are used interchangeably with the term "at least one". The phrases "at least one of" and "comprises at least one of" followed by a list refers to any one of the items in the list and any combination of two or more items in the list. All numerical ranges are inclusive of their endpoints and non-integral values between the endpoints unless otherwise stated.

The terms "first", "second", and "third" are used in this disclosure. It will be understood that, unless otherwise noted, those terms are used in their relative sense only. For these components, the designation of "first", "second", and "third" may be applied to the components merely as a matter of convenience in the description of one or more of the embodiments.

The terms "multiple" and "a plurality" refer to more than one.

The term "opening" should be understood to be a void space in the mechanical fastener material that is surrounded by the mechanical fastener web. One opening is typically enclosed by two multiple strands.

The term "web" can refer to a continuous or running web, sometimes having an indefinite length. A web can typically be handled in a roll-to-roll process. The term "machine direction" (MD) as used above and below denotes the direction of a running web of material during the manufacturing of the mechanical fastener. When a mechanical fastening strip is cut from a continuous web, the machine direction corresponds to the length "L" of the mechanical fastening strip. As used herein, the terms "machine direction" and "longitudinal direction" are typically used interchangeably. The term "cross-machine direction" (CD) as used above and below denotes the direction which is essentially perpendicular to the machine direction. When a mechanical fastening strip is cut from a continuous web, the cross-machine direction corresponds to the width "W" of the mechanical fastening strip.

The above summary of the present disclosure is not intended to describe each disclosed embodiment or every implementation of the present disclosure. The description that follows more particularly exemplifies illustrative embodiments. It is to be understood, therefore, that the drawings and following description are for illustration purposes only and should not be read in a manner that would unduly limit the scope of this disclosure.

BRIEF DESCRIPTION OF THE DRAWINGS

The disclosure may be more completely understood in consideration of the following detailed description of various embodiments of the disclosure in connection with the accompanying drawings, in which:

FIG. 6A is a schematic top view of another embodiment of a portion of a slit web useful for the methods of making a mechanical fastener disclosed herein;

FIG. 6B is a schematic top view of the portion of the slit web of FIG. 6A after it is directed over a first roller and a series of or third second rollers for some embodiments of the method of making a mechanical fastener disclosed herein;

FIG. 7 is a photograph illustrating twisting of strands of a slit web portion when it is spread apart.

DETAILED DESCRIPTION

Figure 1A:
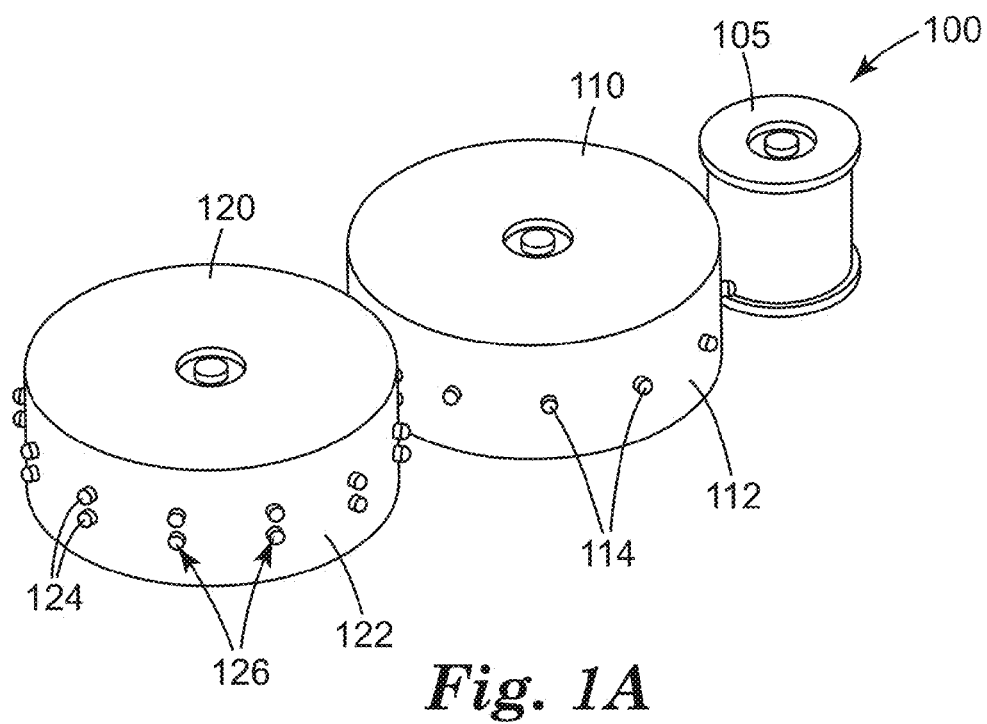
FIG. 1A is a perspective view of an embodiment of the apparatus disclosed herein including a first and second roller useful for the method of making a mechanical fastener disclosed herein.

Reference will now be made in detail to embodiments of the disclosure, one or more examples of which are illustrated in the drawings. Features illustrated or described as part of one embodiment can be used with other embodiments to yield still a third embodiment. It is intended that the present disclosure include these and other modifications and variations.

Figure 1B:
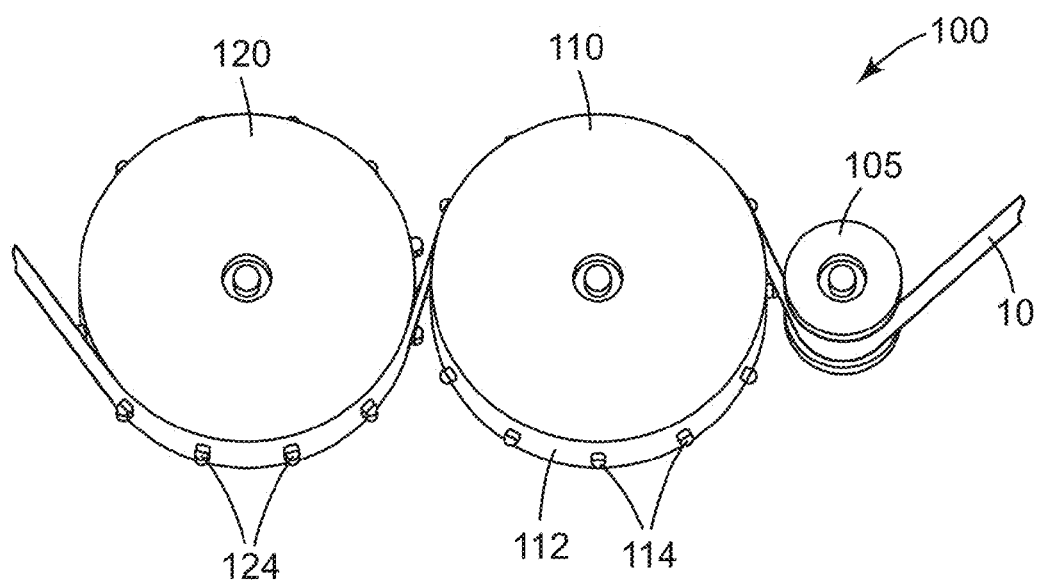
FIG. 1B is a top view showing a slit web being directed over the first and second roller of the apparatus shown in FIG. 1A.

FIGS. 1A and 1B illustrate an embodiment of an apparatus 100 useful for the method of making a mechanical fastener disclosed herein. Apparatus 100 includes a guide roller 105, which can be useful, for example, for guiding the slit web 10 onto the rollers including multiple protrusions. Guide roller 105 can help determine the direction of the slit web 10 and can be useful for adjusting the tension in the slit web 10 as it is directed over the first and second rollers 110 and 120 of apparatus 100.

After guide roller 105, slit web 10 is directed over first roller 110, which has first multiple protrusions 114 around its peripheral surface 112, and then second roller 120, which has multiple paired protrusions 126 around its peripheral surface 122. In the method and apparatus according to the present disclosure, the apparatus may have a series of second rollers 120 or may have one or more third rollers (not shown) described in further detail below. In the illustrated embodiment, the multiple protrusions 114 form a single row centered on the peripheral surface 112 of the first roller 110, and multiple pairs 126 of protrusions 124 form two identical rows centered on the peripheral surface 122 of the second roller 120. When pairs 126 of protrusions 124, for example, two identical rows of protrusions 124, are centered on a second roller in any of the embodiments disclosed herein, it may be understood that each member of the pair 126 is equidistant on opposite sides from the center line of the roller. How the slit web 10 interacts with the protrusions 114 and 124 first and second rollers 110 and 120 is described below in connection with the slit web illustrated in FIGS. 2A through 2D.

In the embodiment shown in FIG. 1B, the slit web 10 can be directed over the first roller 110 such that the mechanical fastening elements face away from the first roller 110 and over the second roller 120 such that the mechanical fastening elements face toward the second roller 120 or vice versa. In embodiments wherein the apparatus 100 includes a series of second rollers, the slit web may be directed over each consecutive roller in the series of second rollers such that the mechanical fastening elements alternate facing toward the roller and then away from the roller. However, in some embodiments of the apparatus and method disclosed herein, it is not necessary for the web 10 to be directed immediately from one roller to the next. Also, in the embodiment shown in FIG. 1B, the multiple protrusions 114 of the first roller 110 intermesh with the multiple pairs of protrusions 124 in gear fashion although in other embodiments described below, the protrusions on one roller may meet the protrusions on the next roller head-to-head.

Figure 2A:
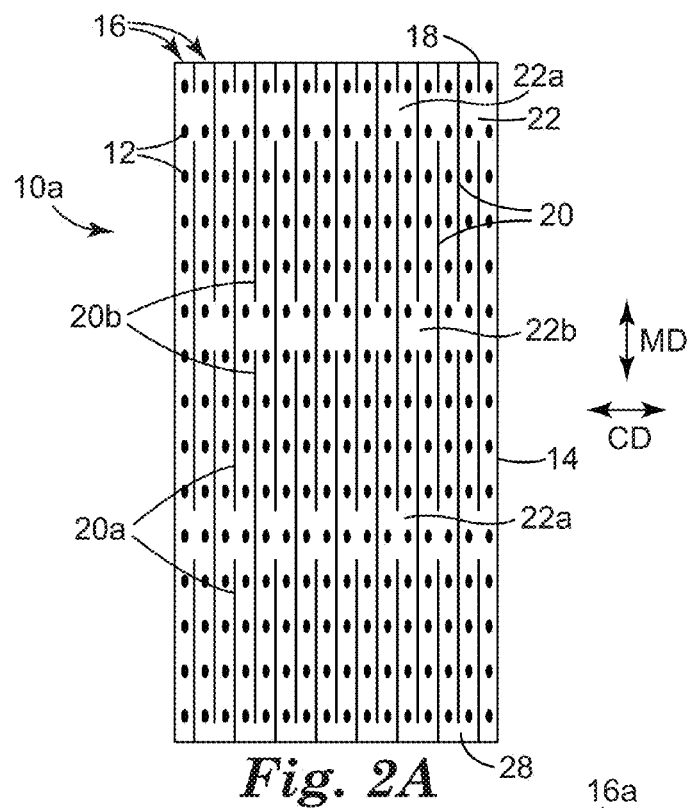
FIG. 2A is a top view of an embodiment of a portion of a slit web useful for the method of making a mechanical fastener disclosed herein.

FIG. 2A illustrates an example of a portion of a slit web 10a with interrupted slits 20 that can be spread using the method disclosed herein. In the illustrated embodiment, the mechanical fastening elements of the slit web 10a are male fastening elements 12. Illustrated slit web 10a has a thermoplastic backing 14 with multiple rows 16 of male fastening elements 12 projecting from a first surface of the backing 14. The first surface of the backing is the surface that is visible in FIG. 2A. The first surface (that is, the surface with mechanical fastening elements) can also be called the first major surface in any of the embodiments disclosed herein. In the illustrated embodiment, the multiple rows 16 of male fastening elements 12 are aligned in the MD although this is not a requirement. The term "row" refers to male fastening elements lined up in a particular direction. The row or line of male fastening elements may be substantially straight.

In the portion of slit web 10a, interrupted slits 20 are cut into the backing between some pairs of adjacent rows 16 of male fastening elements 12. When an interrupted slit is cut between adjacent rows 16 of male fastening elements 12, it typically means that the particular slit does not cross over a row of male fastening elements 12. The illustrated interrupted slits 20 are linear in the same direction "MD" as the multiple rows 16 and extend from the top edge 18 to the bottom edge 28 of the backing 14. The interrupted slits are interrupted by intact bridging regions 22 of the backing 14. The bridging regions 22 are regions where the web is not cut through, and at least a portion of the bridging regions 22 can be considered collinear with interrupted slit 20. The intact bridging regions 22 divide the interrupted slits into a series of spaced apart slit portions 20a. The spaced apart slit portions 20a and 20b and consequently bridging regions 22a and 22b of adjacent interrupted slits are staggered in a direction "CD" perpendicular to the direction "MD" of the interrupted slits 20. The slit portions 20a and 20b are staggered such that bridging region 22b is located substantially midway between bridging regions 22a in the direction "MD". However, in some embodiments, the upstanding posts 12, interrupted slits 20, and bridging regions 22, 22a, and 22b may be positioned in other arrangements. When the slit portions and bridging regions are staggered, the number of bridging regions necessary to make the slit mechanical fastener handle as an integral unit can be minimized.

Generally, for the methods disclosed herein, the interrupted slits 20 extend in the MD. When it is said that an interrupted slit "extends" in the MD, it is meant that the slit is arranged or aligned in that direction or at least predominantly in that direction. The slit may be linear. As used herein a "linear" slit can be defined by two points in a line on the web. The slit may also be substantially linear, which means that the slit can have a slight curvature or slight oscillation. Some oscillation or curvature may result, for example, from the process of slitting a continuous web as would be understood by a person skilled in the art. In some embodiments of mechanical fasteners with male fastening elements made according to the method of the present disclosure, any oscillation or curvature is such that the slit generally does not have a portion that crosses over a row of male fastening elements aligned in the MD. The interrupted slit may also have a wavy or sawtooth pattern with a small amplitude, and such a slit would also be considered to extend in the MD.

The particular arrangement of the bridging regions 22, 22a, and 22b can be designed, for example, based on the desired length of the slits and the amount of spreading desired for the multiple strands 26. Various lengths of bridging regions 22, 22a, and 22b may be useful. In some embodiments, any bridging regions 22 in a given interrupted slit 20 have a combined length in the direction of the interrupted slit of up to 50 (in some embodiments, 40, 30, 25, 20, 15, or 10) percent of the length of the slit web in the MD. In some embodiments, for maximizing the ability of the slit web 10a to spread, it may be desirable to minimize the combined length of the bridging regions in the direction of the interrupted slit. Minimizing the combined length of the bridging regions 22 in the direction of the interrupted slit may be accomplished by at least one of minimizing the length of any particular bridging region 22 or maximizing the distance between bridging regions 22. In some embodiments, the length of one bridging region in the direction of the interrupted slit is up to 3, 2, or 1.5 mm and at least 0.25, 0.5, or 0.75 mm. In some embodiments, the number of bridging regions along the length of the slit web 10a in the direction of the interrupted slit is up to 1.5, 1.25, 1.0, 0.75, 0.60, or 0.5 per cm. The distance between bridging regions 22 in the direction of the interrupted slit may be, for example, at least 0.75, 1.0, 1.25, 1.5, or 1.75 cm. Furthermore, the length of the interrupted slit portions between bridging regions can be adjusted and may be selected to maximize the distance between bridging regions. In some embodiments, the length of the slit portions 20a, 20b is at least 8 (in some embodiments, at least 10, 12, 14, 15, 16, 17, 18, 19, or 20) mm. Typically, the interrupted slits of the slit webs 10a useful for practicing the present disclosure have longer slit regions and shorter bridging regions than perforations that are designed to allow easy separation of two parts of a film.

It is typically useful for the slit portions 20a, 20b to have a regular pattern that repeats down the slit web 10a. The regular pattern is useful, for example, for keeping the slit portions 20a of a particular interrupted slit 20 aligned with the protrusions of first roller 110 or second roller 120 as it rotates as described in further detail below. Accordingly, the regular pattern of slit portions 20a, 20b may repeat with the same frequency as one rotation of first roller 110 or second roller 120. In some embodiments, spacing (e.g., in the MD) between slit portions 20a may be uniform or substantially uniform (that is, the spacing may differ by up to 2 percent, 1 percent, or less than 1 or 0.5 percent) although this is not a requirement.

For any of the embodiments of the method of making a mechanical fastener disclosed herein, the number of interrupted slits and resulting openings may be adjusted depending on the desired spread mechanical fastening web. The interrupted slits may be evenly spaced or unevenly spaced as desired. In some embodiments, there are up to 10, 9, 8, 7, 6, 5, 4, 3, 2, or 1 interrupted slits per 10 mm across the width of the slit web in the CD. Changing the number of interrupted slits across the slit web may be related to the number of rows of male fastening elements between any two adjacent interrupted slits, depending on the density of the male fastening elements on the backing. The number of rows of male fastening elements between any two adjacent interrupted slits may be adjusted depending on the requirements of the application. In some embodiments, there are up to 10, 9, 8, 7, 6, 5, 4, 3, 2 rows, or 1 row of male fastening elements between any two adjacent interrupted slits. Typically, the width dimension of each of the multiple strands formed between interrupted slits is wider than at least the bases of the upstanding posts of the male fastening elements. In some embodiments, there is an interrupted slit between every row or every other row of male fastening elements. In the illustrated embodiment, the interrupted slits 20 are evenly spaced among the rows of male fastening elements 12 although this is not a requirement. For multiple rows 16 of male fastening elements 12 that are evenly spaced, as illustrated, the spacing (e.g., distance in the CD) between multiple rows 16 may differ by up to 10, 5, 2.5, or 1 percent. Likewise, for interrupted slits that are evenly spaced, the spacing (e.g., distance in the CD) between the interrupted slits may differ by up to 10, 5, 2.5, or 1 percent.

Figure 2B:
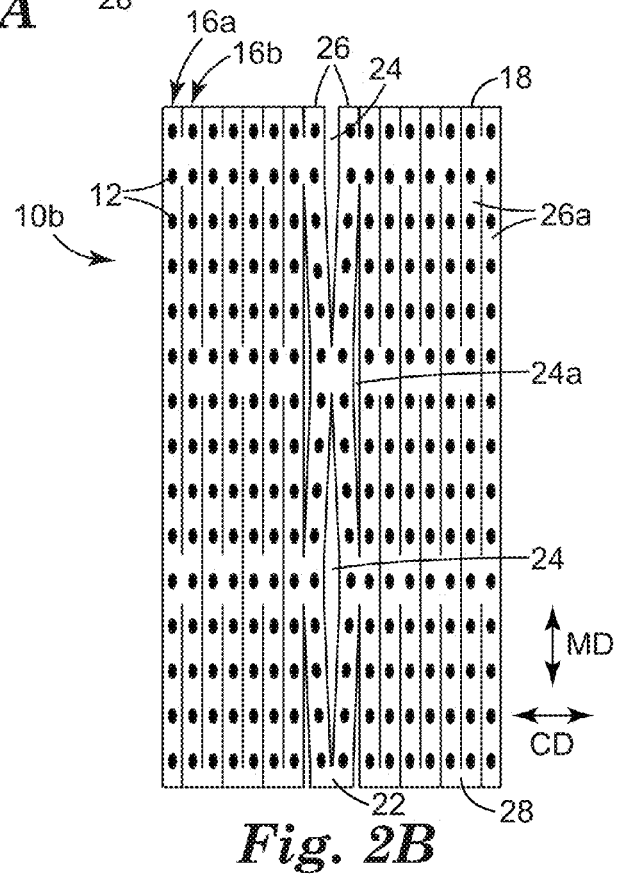
FIG. 2B is a top view of the portion of the slit web of FIG. 2A after it is directed over the first roller of the embodiment of the apparatus shown in FIG. 1A.

FIG. 2B illustrates the effect of spreading the slit web 10a by directing it over the first roller 110 illustrated in FIG. 1A. When the slit web 10a is directed over the first roller 110, multiple protrusions 114 in the first roller 110 are pushed through the slit portions 20b of a first interrupted slit 20 to provide the spread mechanical fastening web 10b. The spread mechanical fastening web 10b has two strands 26 of the slit web attached to each other at intact bridging regions 22 and separated from each other between intact bridging regions 22 to create openings 24. The first interrupted slit may be the center interrupted slit on the slit web.

Figure 2C:
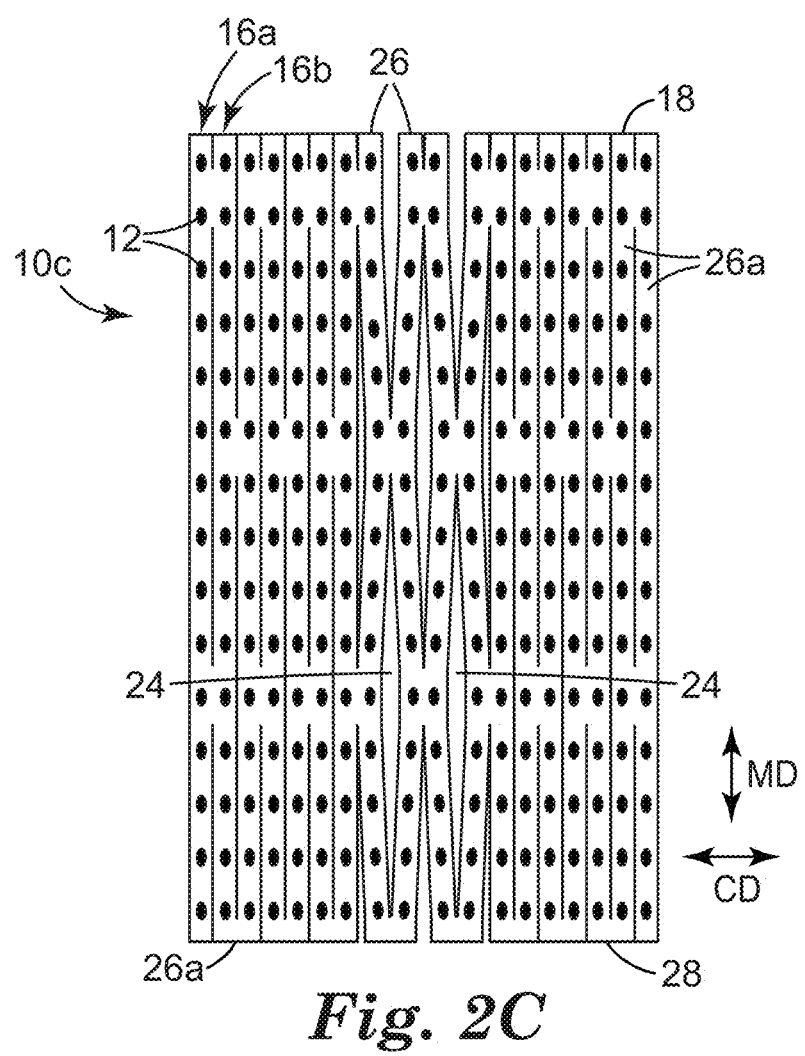
FIG. 2C is a top view of the portion of the slit web of FIG. 2A after it is directed over the first and second rollers of the embodiment of the apparatus shown in FIG. 1A.

FIG. 2C illustrates the effect of spreading the slit web 10b by directing it over the second roller 120 after it was directed over the first roller 110 illustrated in FIG. 1A. When the slit web 10b is directed over the second roller 120, multiple pairs 126 of protrusions 124 in the second roller 120 are pushed through the slit portions 20a, 20b of second and third interrupted slits 20 to provide the spread mechanical fastening web 10c. The second and third of the interrupted slits are on opposite sides of the first interrupted slit and may, in some embodiments, be adjacent to the first interrupted slit. The spread mechanical fastening web 10c has four strands 26 of the slit web attached to each other at intact bridging regions 22 and separated from each other between intact bridging regions 22 to create openings 24.

Figure 4A:
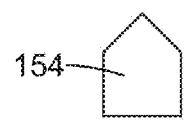
FIGS. 4A and 4B are schematic side views of protrusions that may be useful for various embodiments of the apparatus disclosed herein or for carrying out some embodiments of the method of making a mechanical fastener disclosed herein.
Figure 4B:
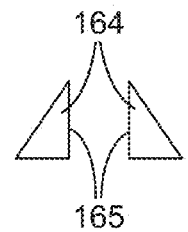

It is also possible, in some embodiments, that the spread mechanical fastening web 10c shown in FIG. 2C, in which a first three of the interrupted slits have been engaged by protrusions, can be made by directing slit web 10a over only a first roller. In these embodiments, the first multiple protrusions may be in the form of a single row centered between and offset from two rows of paired protrusions around the peripheral surface of the first roller. In these embodiments, it may be useful for the protrusions in the single centered row to have a different shape than the paired protrusions. For example, the protrusions in the single centered row may be symmetric as shown, for example, in FIG. 4A, and the paired protrusions may be asymmetric, for example, as shown in FIG. 4B. For the paired protrusions 164 shown in FIG. 4B, sides 165, which are perpendicular to the surface of the roller, may be aligned with the outer two interrupted slits to form openings 24. For the protrusions 154 in the single centered row, the apex of protrusions 154 may be aligned with the center interrupted slit.

Figure 2D:
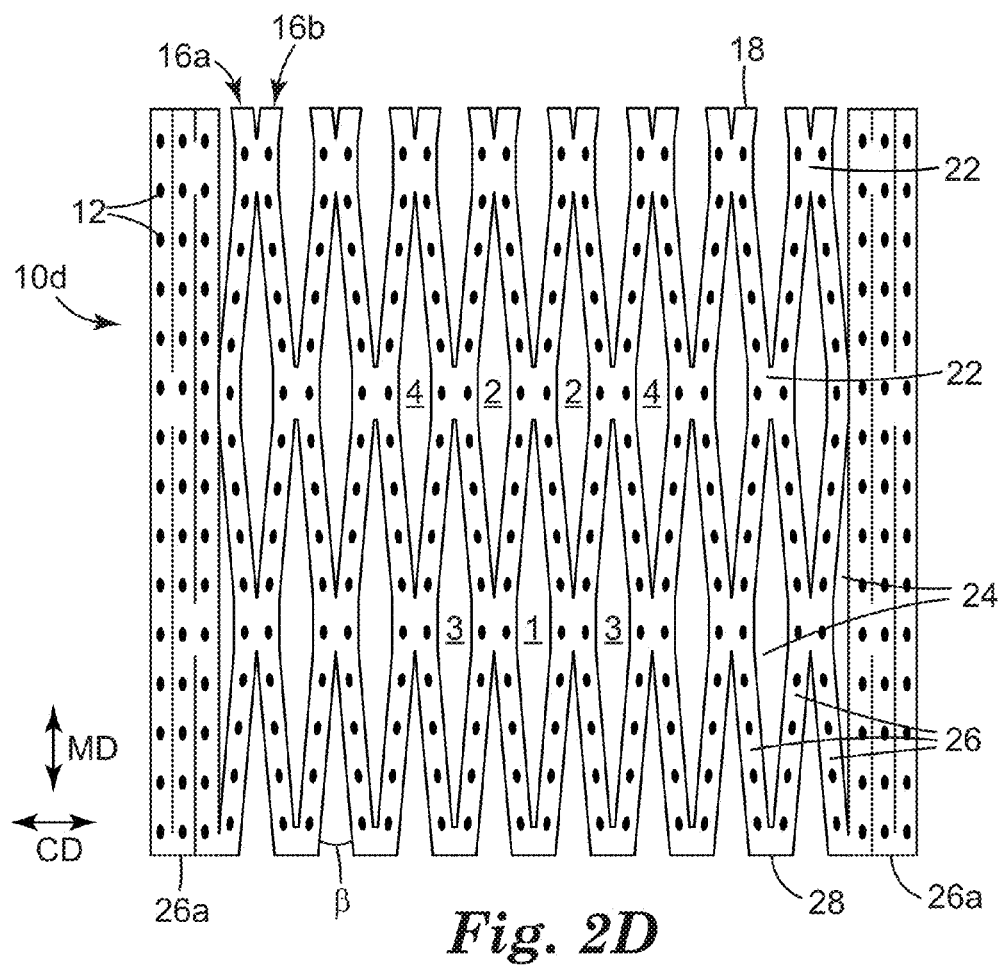
FIG. 2D is a top view of the portion of the slit web similar to FIG. 2A after it is directed over a first roller and a series of second or third rollers for some embodiments of the method of making a mechanical fastener disclosed herein.

FIG. 2D illustrates the effect of spreading the slit web 10b by directing it over a series of second rollers 120 or a series of third rollers after it was directed over the first roller 110 illustrated in FIG. 1A. When the slit web 10b is directed over the series of second rollers 120, multiple pairs 126 of protrusions 124 in each second roller 120 are pushed through the slit portions 20a, 20b of an opposing pair of interrupted slits 20 to provide the spread mechanical fastening web 10d. For each consecutive roller in the series of second rollers 120, the paired protrusions 126 and the opposing pair of the interrupted slits 20 are spaced progressively further apart. In some embodiments, the first interrupted slit is spread on the first roller to provide the openings labeled 1, the two adjacent interrupted slits on either side of the first interrupted slit are spread on the first of the series of second rollers to provide openings labeled 2, the next two interrupted slits closest to the two adjacent interrupted slits are spread on the next in a series of second rollers to provide the openings labeled 3, and so on until the desired amount of interrupted slits has been spread. The spread mechanical fastening web 10d has multiple strands 26 of the slit web attached to each other at intact bridging regions 22 and separated from each other between intact bridging regions 22 to create openings 24.

Figure 3A:
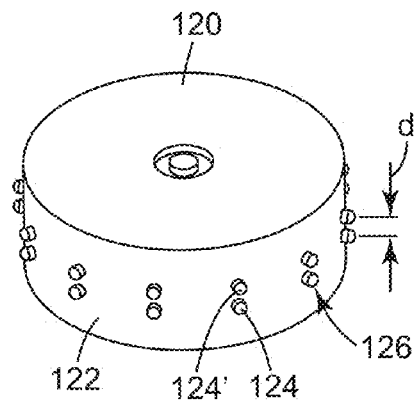
FIG. 3A is a perspective view of a first roller or a second roller in various embodiments of the apparatus disclosed herein or useful for carrying out some embodiments of the method of making a mechanical fastener disclosed herein.
Figure 3B:
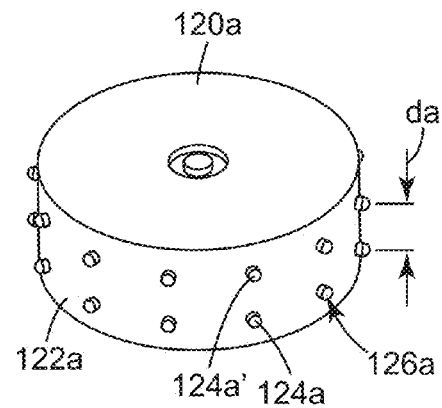
FIG. 3B is a perspective view of a second roller, which may be in a series of second rollers, in some embodiments of the apparatus disclosed herein or useful for carrying out some embodiments of the method of making a mechanical fastener disclosed herein.

The spacing between the protrusions 124, 124' in a pair of protrusions 126 in a second roller may be more clearly shown in FIG. 3A. As shown in FIG. 3A, for each pair 126 of protrusions on the second roller 120, the protrusions 124, 124' on the peripheral surface 122 of the second roller 120 are spaced a distance "d" from each other. FIG. 3B illustrates a second roller 120a which is later in a series of second rollers than second roller 120. For each pair 126a of protrusions 126a on the peripheral surface 122a of the second roller 120a, the distance "da" between the protrusions 124a and 124a' is greater than the distance "d" between the protrusions 124 and 124' in the second roller 120.

Figure 3C:
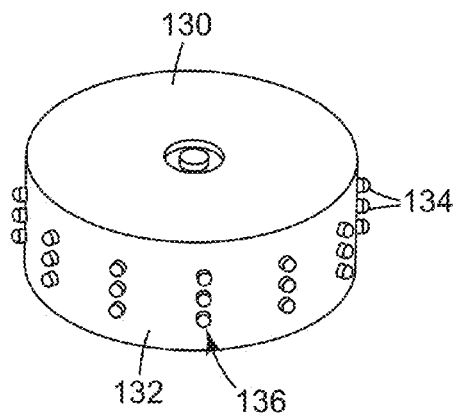
FIGS. 3C and 3D are perspective views of third rollers, which may be in a series of third rollers in some embodiments of the apparatus disclosed herein or useful for carrying out some embodiments of the method of making a mechanical fastener disclosed herein.
Figure 3D:
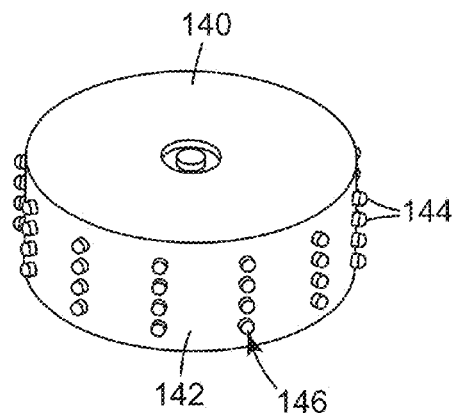

Referring again to FIG. 2D, in embodiments where the apparatus and method disclosed herein include a series of third rollers, the first interrupted slit can be spread on the first roller to provide the openings labeled 1, the two adjacent interrupted slits on either side of the first interrupted slit can be spread on a second roller to provide openings labeled 2, and the next roller 130, which can be the first in a series of third rollers, may have a group 136 of three protrusions 134 around its peripheral surface 132 as shown in FIG. 3C. The middle of the three protrusions 134 can fit into the opening labeled 1 while the outer protrusions in the group 136 can push through the slits on either side to create openings 3. Another third roller 140 in a series of third rollers may have a group 146 of four protrusions 144 around its peripheral surface 142 as shown in FIG. 3D. The middle two of the protrusions 144 can fit into the openings labeled 2 while the outer protrusions in the group 146 can push through the slits on either side to create openings 4. This process can be repeated on additional third rollers until the desired number of interrupted slits has been spread.

Figure 3E:
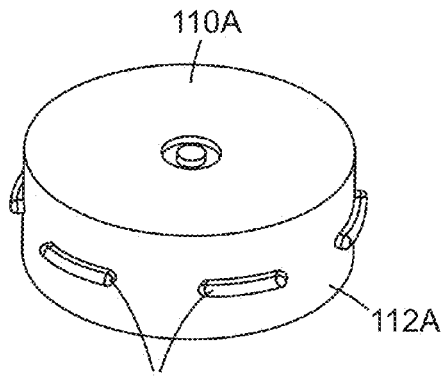
FIG. 3E is a perspective view of another embodiment of a first roller of the apparatus disclosed herein or useful in the method of making a mechanical fastener disclosed herein.

The protrusions in the first and second rollers may have a variety of shapes. In the embodiments illustrated in FIGS. 1A, 1B, and 3A through 3D, the protrusions 114, 124, 124', 124a, 124a', 134, and 144 are in the form of pins, which may have a cylindrical shape at the base attached to the peripheral surfaces 112, 122, 122a, 132, and 142. The top of the pin can be narrower than the base and can be rounded or dome shaped as shown in FIGS. 1A, 1B, and 3A through 3D. The top of the pin may also be pointed as shown in pin 154 of FIG. 4A. The shape of the protrusions may also be as shown in FIG. 3E. In FIG. 3E, protrusions 114A on the peripheral surface 112A of first roller 110A are in the form of ribs or ridges. The extended length of the protrusions 114A may be useful, for example, for keeping the protrusions 114A aligned with the slit portions 20b in the slit web during a running web process. Elongated protrusions such as ribs 114A in other embodiments may not have uniform thickness. For example, they may be generally in the shape of a rhombus or other geometrical shape of the openings to be made in the slit web.

In any of the embodiments described above, the number of rollers used in the series of second rollers in the method or apparatus according to the present disclosure may be selected to provide openings between all of the multiple strands 26 or selected so that not all of the multiple strands 26 are spread between the bridging regions 22. Typically, the number of rollers (including first and second or third rollers) useful for opening a desired number (n) of interrupted slits in a slit web is (n+1) divided by 2. However, if the first roller engages a first three of the interrupted slits as described above, the number of rollers can be n divided by 2. Similarly, the number of second rollers typically useful for opening a desired number (n) of opposing pairs of interrupted slits in a slit web is n divided by 2. In the embodiment illustrated in FIG. 2D, at least two strands 26a, including at least two rows of male fastening elements on each edge of the mechanical fastener, are not separated. This may be advantageous in some embodiments, for example, to provide a reticulated mechanical fastening strip or patch with a straight edge.

Figure 2E:
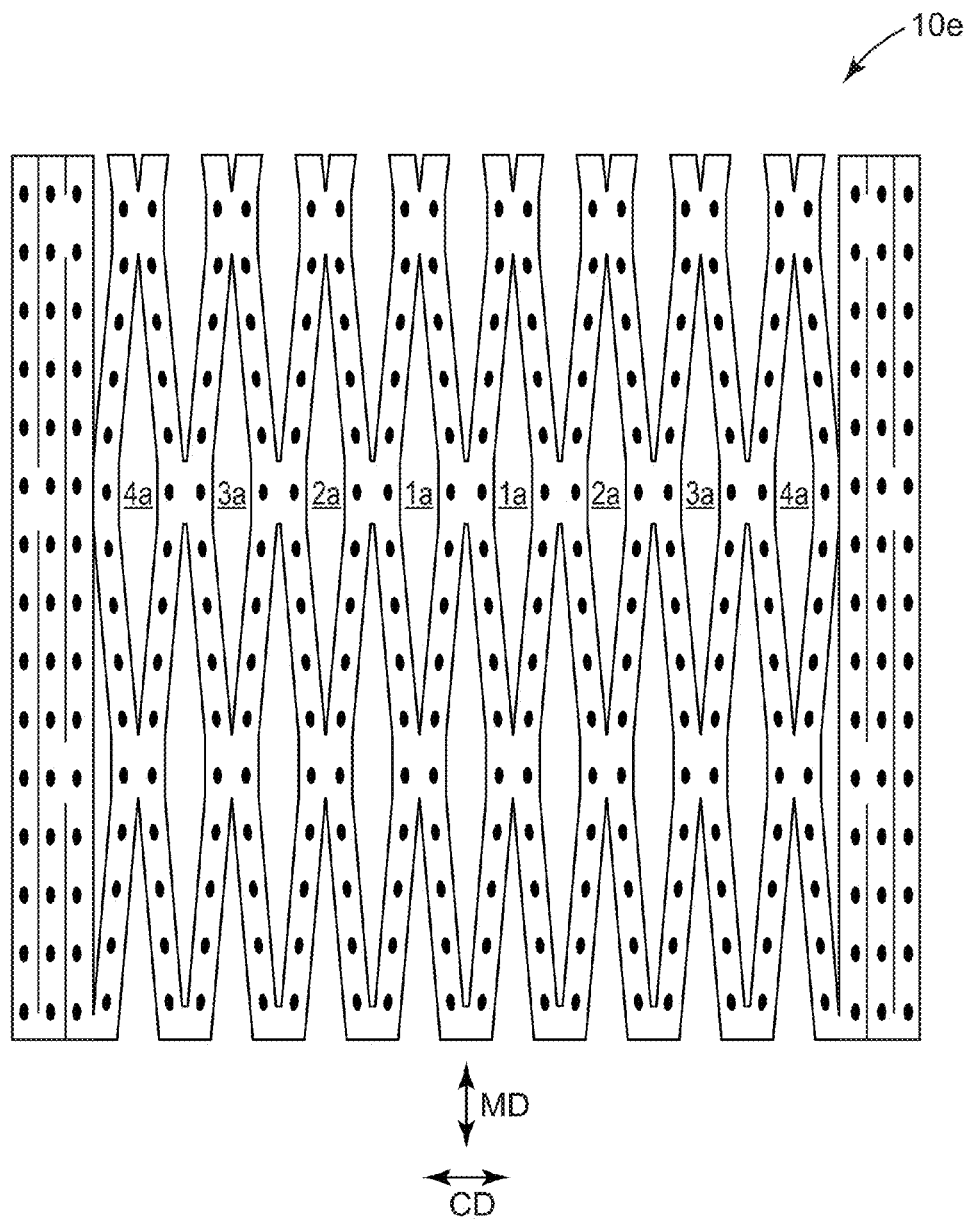
FIG. 2E is a top view of the portion of the slit web similar to FIG. 2A after it is directed over a first roller and a series of second or third rollers for some embodiments of the method of making a mechanical fastener disclosed herein with FIG. 2E showing a different way rollers with protrusions can open interrupted slits than FIG. 2D.

In some embodiments, the first roller may be similar to roller 120 shown in FIG. 3A. That is, it can have first multiple protrusions in the form of multiple pairs 126 of protrusions 124 and 124' forming two identical rows around the peripheral surface 122 of the first roller to push through the consecutive slit portions of a first two of the interrupted slits. In these embodiments, the next roller may be a second roller 120a as shown in FIG. 3B or a third roller 140 as shown in FIG. 3D. In either of these embodiments, the slit web may be spread as shown in FIG. 2E. In this illustrated embodiment, the first roller pushes through consecutive slit portions of a first two interrupted slits to provide the openings labeled 1a, and two interrupted slits on either side of the first two interrupted slits are spread on the next roller, which may be second roller 120a or third roller 140, to provide openings labeled 2a. In embodiments where third roller 140 is used, the middle two of the protrusions 144 can fit into the openings labeled 1a while the outer protrusions in the group 146 can push through the slits on either side to create openings 2a. The next two rollers in a series of second rollers or a series of third rollers push through consecutive slit portions in more interrupted slits in a similar fashion to provide the openings labeled 3a and 4a, and so on until the desired amount of interrupted slits has been spread. In these embodiments, the protrusions that push through the consecutive slit portions in the interrupted slits to be opened may advantageously have an asymmetric shape, for example, as shown for protrusions 164 in FIG. 4B. For the paired protrusions 164 shown in FIG. 4B, sides 165, which are perpendicular to the surface of the roller, may be aligned with the interrupted slits to form openings 24. Also, in these embodiments, the protrusions on one roller may meet the protrusions on the next roller in the series head-to-head instead of in a gear-like fashion.

Although slit web 10e shown in FIG. 2E has a centered interrupted slit, the embodiments described in connection with FIG. 2E may also be useful, for example, when the slit web is not provided with an interrupted slit in the center of the web. These embodiments are also useful when it is desirable to use a lower number of rollers in the method described herein. For example, while the protrusions in the rollers in the embodiments described in connection with FIG. 2E only push through consecutive slit portions of every other interrupted slit and not adjacent interrupted slits, the staggered consecutive portions in the interrupted slits that are not engaged by protrusions may still be opened, for example, by the movement of the multiple strands caused by the protrusions. This effect is illustrated in FIG. 2B, for example, where the creation of openings 24 in the slit web causes movement of the strands 26 that creates the smaller openings 24a. A combination of the opening patterns shown in FIGS. 2D and 2E may also be useful.

The method according to the present disclosure typically increases the width of the slit web (that is, the dimension in the CD). The increase in width may be determined, for example, by the width dimension of the protrusions and the number of rollers in the series of second rollers. In some embodiments, the width of the spread mechanical fastening web is at least 5, 10, 15, 20, or 25 percent greater than the input slit web. In some embodiments, the width of the spread mechanical fastening web is up to 40, 50, 75, 100, or 150 percent greater than the input slit web.

In any of the embodiments described above, a number of techniques may be useful for pushing the multiple protrusions 114 of the first roller and the multiple pairs 126 of protrusions 124 of the one or more second or third rollers through the slit portions 20a and 20b of the web. In some embodiments, tension applied in the machine direction can push the protrusions through the slit portions as the slit web moves around the roller. In some embodiments, vacuum applied on the slit web (e.g., from within the first and/or second roller(s) 110, 120) can help the protrusions to push through the slit portions of the web. In some embodiments, air blown on the slit web (e.g., using an air knife) can help to push web toward the roller and the protrusions through the slit portions. In some embodiments, the first roller, the second roller, and/or the third roller in any of the embodiments of the method or apparatus disclosed herein can be paired with a mating roller to form a nip. The mating roller can be formed with depressions to accept the protrusions in the first, second, and/or third roller so that when the slit web is moved through the nip, the protrusions are forced through the slit portions into the depressions of the mating roll.

While FIGS. 2A through 2D illustrate a backing 14 with male fastening elements 12, it should be understood that a loop material can be slit to provide slit web 10a and spread with the first roller and a series of second rollers or third rollers in the same manner to the same extent as spread mechanical fastening webs 10b through 10e.

Figure 5A:
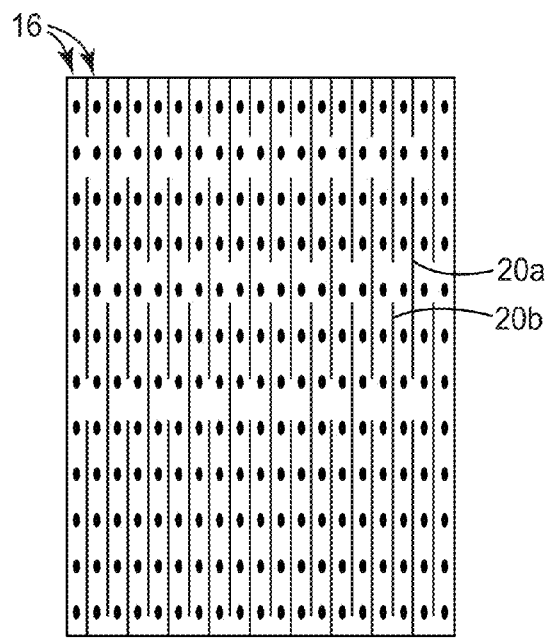
FIG. 5A is a top view of another embodiment of a portion of a slit web useful for the methods of making a mechanical fastener disclosed herein.
Figure 5B:
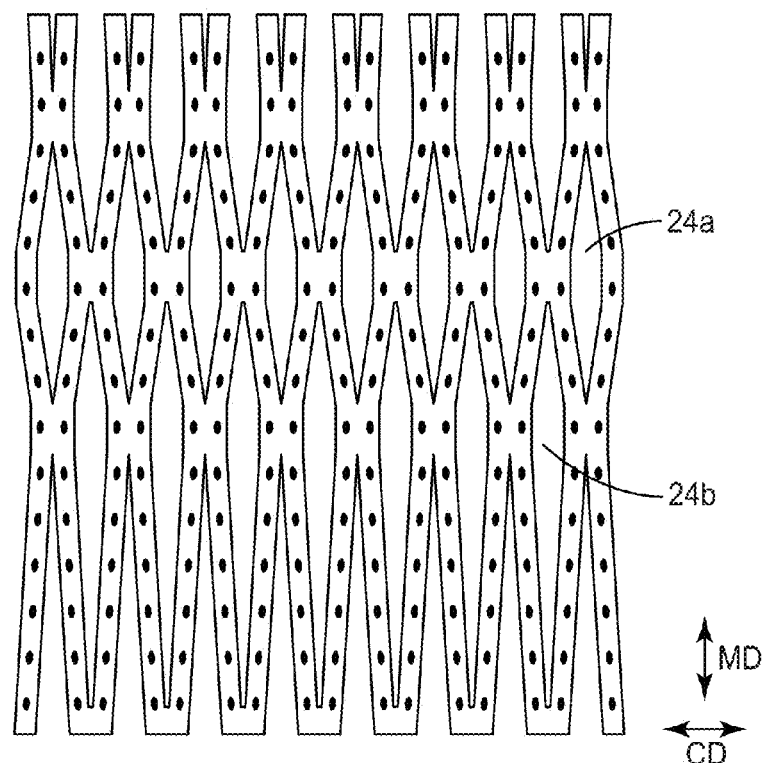
FIG. 5B is a top view of a portion of the slit web similar to FIG. 2A after it is directed over a first roller and a series of second or third rollers for some embodiments of the method of making a mechanical fastener disclosed herein.

FIG. 5A illustrates an exemplary slit web portion having mechanical fastening elements, which is similar to the portion of slit web 10a shown in FIG. 2A. However, in the embodiment shown in FIG. 5A, slit portions 20a have different lengths than slit portions 20b of adjacent slits, which results in openings 24a and 24b having different sizes after the slit web is spread on a first roller and a series of second or third rollers as shown in FIG. 5B. That is, openings 24a are shorter in the MD than openings 24b. The slit portions of the smaller size 20a and slit portions of the larger size 20b each may be aligned with each other across the slit web as shown in FIG. 5A. Or in other embodiments, slits of the same size may be offset relative to each other in a regular pattern. Furthermore, referring again to FIG. 2A, the length of the bridging regions 22 may be made to vary within a strand 26 or between strands 26 as desired for a particular application or appearance. Although FIGS. 5A and 5B illustrate mechanical fasteners with male fastening elements, the same slitting pattern and spreading with a first roller and a series of second or third rollers can be carried out with a loop material.

FIG. 6A illustrates an exemplary slit web having mechanical fastening elements, which is similar to the slit mechanical fastener 10a shown in FIG. 2A. However, in the embodiment shown in FIG. 6A, slit portions 20e have different lengths than slit portions 20f, which results in openings 24c and 24d having different sizes after the slit web is spread on a first roller and a series of second or third rollers as shown in FIG. 6B. In contrast to the embodiment shown in FIGS. 5A and 5B, which illustrates interrupted slits with slit portions of different lengths in the MD and the corresponding resulting openings, FIGS. 6A and 6B illustrate patterns of slit portions of different lengths in different zones in the CD of the slit web. The multiple strands 26c and 26d have a different appearance from each other in the same spread mechanical fastening web, for example, multiple strands 26c and 26b zig-zag or undulate with a different wavelength and amplitude. The slit web and the spread mechanical fastening web shown in FIGS. 6A and 6B, respectively, may include male or female mechanical fastening elements (not shown).

For any of the embodiments of the method of making a mechanical fastener disclosed herein, the openings formed by the separation of the multiple strands between at least some of the bridging regions are in the form of a repeating pattern of geometric shapes. In the illustrated embodiments, the geometric shapes are polygons, which may be quadrilaterals such as rhombuses. In some embodiments of the spread mechanical fastening web, including the embodiment shown in FIG. 2D, the multiple strands of the web attached to each other at least at some of the intact bridging regions form an angle β of less than 90 degrees, in some embodiments, up to 60 degrees, 45 degrees, or 20 degrees, and in some embodiments, in a range from 0.5 to 20 degrees. In some embodiments, curved lines may be used, which can result in crescent shaped openings after spreading. As shown in FIG. 6B, there may be more than one repeating pattern of geometric shaped openings. The openings may be evenly spaced or unevenly spaced as desired. For openings that are evenly spaced, the spacing (e.g., distance in CD) between the openings may differ by up to 10, 5, 2.5, or 1 percent.

For any of the slit webs shown in FIGS. 2A, 5A, and 6A and in other embodiments, first, second, and/or third rollers can be designed to align the multiple protrusions to the slit portions of the slit web so that the protrusions are able to push through the slit portions to provide spread mechanical fastening webs shown in FIGS. 2B through 2D, 5B, and 6B, for example. Accordingly, the protrusions on the first, second, and third rollers can be spaced in any desired pattern to spread the desired slit web. Furthermore, first, second, and/or third rollers can be designed to have any desired size to fit the desired width of the slit web in the CD. For example, the rollers can be made to fit a slit web in a range from 1 cm to 10 cm, 1 cm to 5 cm, or 1 cm to 3 cm wide.

In some embodiments, the slit web useful in the method disclosed herein or the resulting spread mechanical fastening web are made of a thermoplastic material. Suitable thermoplastic materials mechanical fasteners include polyolefin homopolymers such as polyethylene and polypropylene, copolymers of ethylene, propylene and/or butylene; copolymers containing ethylene such as ethylene vinyl acetate and ethylene acrylic acid; polyesters such as poly(ethylene terephthalate), polyethylene butyrate and polyethylene napthalate; polyamides such as poly(hexamethylene adipamide); polyurethanes; polycarbonates; poly(vinyl alcohol); ketones such as polyetheretherketone; polyphenylene sulfide; and mixtures thereof. Typically, the thermoplastic is a polyolefin (e.g., polyethylene, polypropylene, polybutylene, ethylene copolymers, propylene copolymers, butylene copolymers, and copolymers and blends of these materials).

In the embodiments of the slit web useful in the method disclosed herein or the resulting spread mechanical fastening web that includes male fastening elements, the backing and the male fastening elements are typically integral (that is, formed at the same time as a unit, unitary). Upstanding posts on a backing can be made, for example, by feeding a thermoplastic material onto a continuously moving mold surface with cavities having the inverse shape of the posts. The thermoplastic material can be passed between a nip formed by two rolls or a nip between a die face and roll surface, with at least one of the rolls having the cavities. The cavities may be in the inverse shape of a capped post having a loop-engaging head or may be in the inverse shape of a post without loop-engaging heads (e.g., a precursor to a male fastening element). Pressure provided by the nip forces the resin into the cavities. In some embodiments, a vacuum can be used to evacuate the cavities for easier filling of the cavities. The nip typically has a large enough gap such that a coherent backing is formed over the cavities. The mold surface and cavities can optionally be air or water cooled before stripping the integrally formed backing and upstanding hook elements from the mold surface such as by a stripper roll. If the posts formed upon exiting the cavities do not have loop-engaging heads, loop-engaging heads could be subsequently formed into hooks by a capping method as described in U.S. Pat. No. 5,077,870 (Melbye et al.). Typically, the capping method includes deforming the tip portions of the hook elements using heat and/or pressure. The heat and pressure, if both are used, could be applied sequentially or simultaneously.

Suitable tool rolls include those formed from a series of plates defining a plurality of post-forming cavities about its periphery such as those described, for example, in U.S. Pat. No. 4,775,310 (Fischer). Cavities may be formed in the plates by drilling or photoresist technology, for example. Other suitable tool rolls may include wire-wrapped rolls, which are disclosed along with their method of manufacturing, for example, in U.S. Pat. No. 6,190,594 (Gorman et al.). Another exemplary method for forming a thermoplastic backing with upstanding posts includes using a flexible mold belt defining an array of upstanding post-shaped cavities as described in U.S. Pat. No. 7,214,334 (Jens et al.). Yet other useful methods for forming a thermoplastic backing with upstanding posts can be found in U.S. Pat. No. 6,287,665 (Hammer), U.S. Pat. No. 7,198,743 (Tuma), and U.S. Pat. No. 6,627,133 (Tuma).

The male fastening elements may have loop-engaging heads that have an overhang or may be upstanding posts having distal tips that can be formed into loop-engaging heads, if desired. The term "loop-engaging" as used herein relates to the ability of a male fastening element to be mechanically attached to a loop material. Generally, male fastening elements with loop-engaging heads have a head shape that is different from the shape of the post. For example, the male fastening element may be in the shape of a mushroom (e.g., with a circular or oval head enlarged with respect to the stem), a hook, a palm-tree, a nail, a T, or a J. The loop-engageability of male fastening elements may be determined and defined by using standard woven, nonwoven, or knit materials. A region of male fastening elements with loop-engaging heads generally will provide, in combination with a loop material, at least one of a higher peel strength, higher dynamic shear strength, or higher dynamic friction than a region of posts without loop-engaging heads. Male fastening elements that have "loop-engaging overhangs" or "loop-engaging heads" do not include ribs that are precursors to fastening elements (e.g., elongate ribs that are profile extruded and subsequently cut to form male fastening elements upon stretching in the direction of the ribs). Such ribs would not be able to engage loops before they are cut and stretched. Such ribs would also not be considered upstanding posts. Typically, male fastening elements that have loop-engaging heads have a maximum thickness dimension (in either dimension normal to the height) of up to about 1 (in some embodiments, 0.9, 0.8, 0.7, 0.6, 0.5, or 0.45) millimeter. In some embodiments, the male fastening elements have a maximum height (above the backing) of up to 3 mm, 1.5 mm, 1 mm, or 0.5 mm and, in some embodiments a minimum height of at least 0.05 mm, 0.1 mm, or 0.2 mm. In some embodiments, the upstanding posts have aspect ratio (that is, a ratio of height to width at the widest point) of at least about 2:1, 3:1, or 4:1.

In some embodiments of a slit web having male fastening elements useful for practicing the present disclosure, at least a portion of each loop-engaging overhang (e.g., at the cap or head) extends at a nonzero angle to the MD. In some embodiments, each upstanding post has a cap with loop engaging overhangs extending in multiple (i.e., at least two) directions. For example, the upstanding post may be in the shape of a mushroom, a nail, a palm tree, or a T. In some embodiments, the upstanding posts are provided with a mushroom head (e.g., with an oval or round cap distal from the thermoplastic backing). In other embodiments, loop-engaging overhangs (e.g., at the cap or head) on the upstanding posts of the slit web extend parallel to the MD. For example, the upstanding posts may have the shape of a J (e.g., as shown in U.S. Pat. No. 5,953,797 (Provost et al.).

In spread mechanical fastening web 10b, 10c, and 10b illustrated in FIGS. 2B-2D, the male fastening elements 12 on a first strand 26 are arranged in a series 16a that is non-parallel to a series 16b of male fastening elements 12 on a second, adjacent strand 26. The series 16a and 16b of multiple upstanding posts and the multiple strands themselves from which they project can undulate or zig-zag along the length of the spread mechanical fastening web 10b, 10c, or 10d, for example, from the top edge 18 to the bottom edge 28. In the illustrated embodiment, the caps visible on the male fastening elements 12 have an oval shape, and these caps are oriented in different directions along the multiple strands 26 in the MD. When the caps are circular in shape, it may not be observed that the caps are oriented in different directions along the multiple strands 26, unless the cap is marked in some way. In the illustrated embodiment, the caps on a first strand 26 are oriented in a different direction than the caps on a second, adjacent strand 26. In embodiments in which slit web 10a includes male fastening elements having loop-engaging overhangs aligned only parallel to the MD, spreading the slit web 10a typically results in the loop-engaging overhangs oriented in different directions along the multiple strands in the MD as shown in FIG. 2D. When loop-engaging overhangs are oriented in multiple directions (e.g., not only one direction such as the machine direction), enhanced engagement of a loop material may advantageously result.

Loop materials useful for practicing some embodiments of the present disclosure (e.g., when the mechanical fastener is a loop material) can be any suitable material that interlocks with corresponding hook fastening elements. In some embodiments, the loop fastening elements are typically formed from knitted fabrics, woven fabrics, or non-woven fabrics. The term "non-woven" refers to a material having a structure of individual fibers or threads that are interlaid but not in an identifiable manner such as in a knitted fabric. Examples of non-woven webs include spunbond webs, spunlaced webs, airlaid webs, meltblown web, and bonded carded webs. The spread mechanical fastening web prepared by the method disclosed herein may include fiber loops projecting from a knitted, woven, or non-woven backing or may be extrusion-bonded, adhesive-bonded, and/or sonically-bonded fiber loops. Useful loop materials may be made of natural fibers (e.g., wood or cotton fibers), synthetic fibers (e.g., thermoplastic fibers), or a combination of natural and synthetic fibers. Exemplary materials for forming thermoplastic fibers include polyolefins (e.g., polyethylene, polypropylene, polybutylene, ethylene copolymers, propylene copolymers, butylene copolymers, and copolymers and blends of these polymers), polyesters, and polyamides. The fibers may also be multi-component fibers, for example, having a core of one thermoplastic material and a sheath of another thermoplastic material.

In some embodiments, the loop material comprises a fibrous layer disposed on a backing. Suitable backings include textiles, paper, thermoplastic films (e.g., single- or multilayered films, coextruded films, laterally laminated films, or films comprising foam layers), and combinations thereof. For thermoplastic backings, the thermoplastic can be any of those described above in connection with a thermoplastic backing having male fastening elements. Exemplary suitable loop materials are described, for example, in U.S. Pat. No. 5,256,231 (Gorman et al.) and U.S. Pat. No. 5,389,416 (Mody et al.). As described in U.S. Pat. No. 5,256,231 (Gorman et al.), the fibrous layer in a loop material according to some embodiments disclosed herein comprises arcuate portions projecting in the same direction from spaced anchor portions on the backing.

In embodiments wherein the mechanical fastening web either has male fastening elements or a fibrous layer on a backing, the thickness of the backing may be up to about 400, 250, 150, 100, 75 or 50 micrometers, depending on the desired application. In some embodiments, the thickness of the backing is in a range from 30 to about 225 micrometers, from about 50 to about 200 micrometers, or from about 100 to about 150 micrometers. In some embodiments wherein the backing is a thermoplastic backing, the thermoplastic backing has stretch-induced molecular orientation, for example, when the thermoplastic backing is stretched after formation of upstanding posts. In other embodiments, the thermoplastic backing or the spread mechanical fastening web is not provided with macroscopic stretch-induced molecular orientation in the direction of the interrupted slits or in the direction of spreading. In these embodiments, there may be some stress-induced orientation localized in the bridging regions.

For any of the aforementioned embodiments of the method according to the present disclosure, providing a slit web having mechanical fastener elements with interrupted slits can be carried out in a variety of ways. For example, rotary die cutting of a continuous web having male fastening elements or loops as described above may be useful. Interrupted slits can be made, for example, by using rotary cutting blades having gaps to form the bridging regions. The height of the blade in the gaps may be adjusted to allow for the bridging regions to be partially cut or not cut at all, depending on the desired embodiment. Other cutting methods (e.g., laser cutting) may also be useful. Cutting can be performed from either surface of the continuous web. A slit may be cut "through" the web having mechanical fastening elements, which means that the slit cuts through the entire thickness of the web. In other embodiments, the slit may be a partial-depth slit as long as the protrusions on the first, second, and/or third rollers can push through the partial depth slit. The partial-depth slit may penetrate, for example, 80, 85, or 90 percent of the thickness of the web or more, which means the solution to the equation:

(depth of the slit divided by the thickness of the web) multiplied by 100 is at least 80, 85, or 90 in some embodiments. Other methods of slitting a web can be found, for example, in U.S. Pat. Appl. Pub. No. 2011/0313389 (Wood et al.).

When male fastening elements are formed as described above, for example, where a thermoplastic material is fed onto a continuously moving mold surface with cavities having the inverse shape of upstanding posts, slitting the web and spreading the slit web according to the method disclosed herein can be carried out before or after a capping step is carried out to form loop-engaging heads. Also, deforming the distal tip to form a cap can be carried out, for example, after slitting through the web but before spreading the slit web; after spreading the slit web but before annealing (described below); or after annealing as desired.

The method and apparatus of the present disclosure can typically spread a slit mechanical fastening web while advantageously not allowing all of the multiple strands of the spread mechanical fastening web to twist out-of-plane. The twisting out-of-plane that can result when spreading a slit web is shown in the photograph of FIG. 7. Pieces of loop material were attached to the edges of a slit mechanical fastener web portion with male fastening elements such as that shown in FIG. 2A. When the pieces of loop material were pulled apart, the individual strands of the slit web tended to twist out of the plane of the web as shown in FIG. 7. This twisting out-of-plane may present challenges when the spread web is to be cut and used as a mechanical fastening patch, for example. The amount of out-of-plane twisting is typically affected, for example, by the extent to which the slit backing is spread.

A number of features of the method and apparatus according to the present disclosure can help control the out-of-plane twisting tendency of the slit web. For example, in some embodiments, the extent of spreading can be controlled, as described above, by the size of the protrusion and the number of rollers used in the series of second rollers. Also, in some embodiments, tension applied in the machine direction that can push the protrusions through the slit web can exert a force on the slit web in the direction normal to the slit web that helps to keep the multiple strands in plane. In these embodiments, the method disclosed herein may be considered to maintain or constrain at least some of the multiple strands in a substantially coplanar arrangement. A substantially "coplanar" arrangement refers to the strands occupying substantially the same plane. The term "substantially" in this regard can mean that at least some of the multiple strands can be twisted out of plane by up to 15, 10, or 5 degrees. The phrase "at least some" with regard to the multiple strands being constrained refers to at least 25, 50, 75, or 90 percent or more of the multiple strands being constrained.

In some embodiments, the method according to the present disclosure further comprises heating the spread mechanical fastening web. In some embodiments, the method according to the present disclosure further comprises annealing the spread mechanical fastening web. In some embodiments, annealing comprises heating the spread mechanical fastening web. In some embodiments, annealing comprises heating and then cooling (e.g., rapidly cooling) the spread mechanical fastening web to maintain its configuration. Heating and/or annealing can be carried out, for example, after the spread mechanical fastening web has been spread to the final desired extent or during or after encountering each of the first and/or second rollers. In some embodiments of the method or apparatus disclosed herein, the first roller and/or any second or third roller, for example, in a series of second or third rollers can be heated. In some embodiments, at least the last second or third roller, for example, in a series of second or third rollers, is heated. Annealing can be useful, for example, depending on the extent of spreading, and can be useful to maintain the openings between multiple strands, for example, when the width of the slit web has been increased by at least 50 percent. Annealing can also be useful, for example, for maintaining at least some of the multiple strands in a substantially coplanar arrangement. In some embodiments, heating is only applied to the second surface of the spread mechanical fastening web (i.e., the surface opposite the first surface from which the mechanical fastening elements project) to minimize any damage to the mechanical fastening elements that may result from heating. Heating may be also carried out on a continuous web, for example, using heated rollers, or using non-contact heating methods such as IR irradiation, hot air treatment (e.g., using an air knife as described above), or by enclosing the apparatus disclosed herein at least partially in a heated chamber.

For any of the embodiments of the method of making a mechanical fastener disclosed herein, the spread mechanical fastening web may be in the form of a roll. The bridging regions interrupting the interrupted slits allow the spread mechanical fastening web to be handled as an integral unit, for example, to be handled in roll form and converted as desired.

Figure 8:
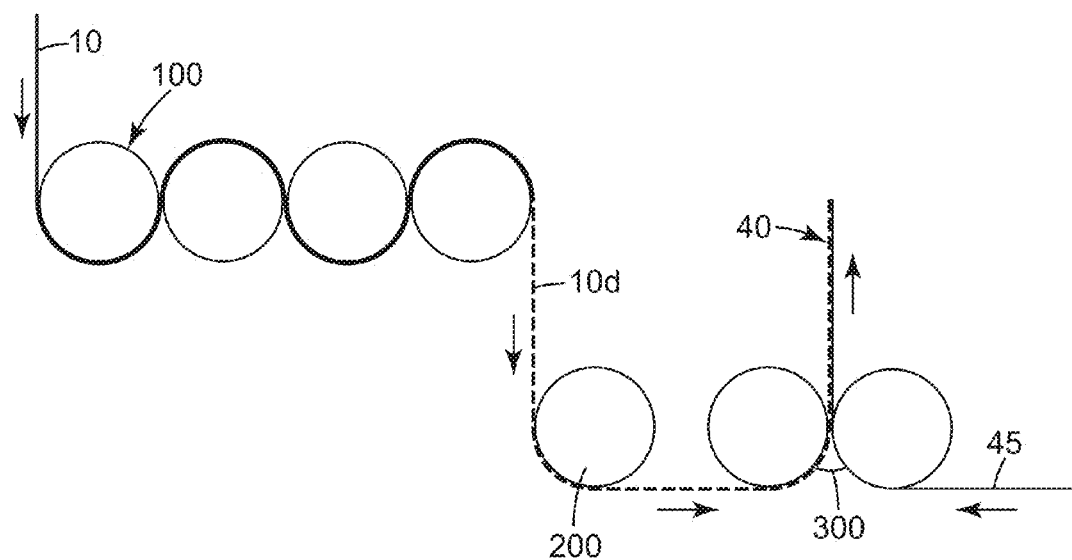
FIG. 8 is a diagrammatical view of an embodiment of apparatus according to the present disclosure useful for carrying out some embodiments of the method of making a mechanical fastener disclosed herein.

Other processes may be useful for facilitating handling or processing the spread mechanical fastening web made by the method or on the apparatus disclosed herein. A diagrammatical representation of an embodiment of an apparatus according to and/or useful for carrying out some embodiments of the method of the present disclosure is shown in FIG. 8. In FIG. 8, slit web 10 is directed over an embodiment of apparatus 100. The illustrated apparatus 100 includes a first roller and three second rollers. After exiting apparatus 100, spread mechanical fastening web 10d can optionally be handled by one or more rollers 200. Roller 200 may be a rotating heated cylinder (or heated roller) as described above. In this case, it may be useful to direct the spread mechanical fastening web onto another roller which is a rotating chilled cylinder to rapidly cool the spread mechanical fastening web. For embodiments in which at least one of the first or second rollers of apparatus 100 is heated, roller 200 may be a rotating chilled cylinder. In some embodiments, roller 200 is a high-friction roller (e.g., comprising a rubbery material), which may be heated or chilled. A high-friction roller may be useful, for example, for holding the spread mechanical fastening web in a spread configuration whether or not the web is annealed. From the high-friction roller, the spread mechanical fastening web may, in some embodiments, be directed to a nip 300, where it is laminated to a carrier web 45 to form a laminate 40.

Although the bridging regions in the spread mechanical fastening web allow it to be handled as an integral unit, it may be useful to laminate the spread mechanical fastening web to a carrier (e.g., even a sacrificial carrier) for ease of handling, for fixing the multiple strands of the spread mechanical fastening web in a spread configuration to maintain the separation between the multiple strands, or for making a fastening laminate for a selected application. The spread mechanical fastening web may be joined to a carrier, for example, by lamination (e.g., extrusion lamination), adhesives (e.g., pressure sensitive adhesives), or other bonding methods (e.g., ultrasonic bonding, compression bonding, or surface bonding).

The carrier 45 may be continuous (i.e., without any through-penetrating holes) or discontinuous (e.g. comprising through-penetrating perforations or pores). The carrier may comprise a variety of suitable materials including woven webs, non-woven webs (e.g., spunbond webs, spunlaced webs, airlaid webs, meltblown web, and bonded carded webs), textiles, plastic films (e.g., single- or multi-layered films, coextruded films, laterally laminated films, or films comprising foam layers), and combinations thereof. In some embodiments, the carrier is a fibrous material (e.g., a woven, nonwoven, or knit material). In some embodiments, the carrier comprises multiple layers of nonwoven materials with, for example, at least one layer of a meltblown nonwoven and at least one layer of a spunbonded nonwoven, or any other suitable combination of nonwoven materials. For example, the carrier may be a spunbond-meltbond-spunbond, spunbond-spunbond, or spunbond-spunbond-spunbond multilayer material. Or, the carrier may be a composite web comprising a nonwoven layer and a dense film layer. Fibrous materials that may provide useful carriers may be made from any of the fibers described above as useful for making loop materials. Useful carriers may have any suitable basis weight or thickness that is desired for a particular application. For a fibrous carrier, the basis weight may range, e.g., from at least about 5, 8, 10, 20, 30, or 40 grams per square meter, up to about 400, 200, or 100 grams per square meter. The carrier may be up to about 5 mm, about 2 mm, or about 1 mm in thickness and/or at least about 0.1, about 0.2, or about 0.5 mm in thickness.

In some embodiments where the spread mechanical fastening web includes a thermoplastic backing (e.g., with upstanding posts or a fibrous layer thereon) the thermoplastic backing can be joined to a fibrous web carrier using surface bonding or loft-retaining bonding techniques. The term "surface-bonded" when referring to the bonding of fibrous materials means that parts of fiber surfaces of at least portions of fibers are melt-bonded to the second surface of the backing, in such a manner as to substantially preserve the original (pre-bonded) shape of the second surface of the backing, and to substantially preserve at least some portions of the second surface of the backing in an exposed condition, in the surface-bonded area. Quantitatively, surface-bonded fibers may be distinguished from embedded fibers in that at least about 65% of the surface area of the surface-bonded fiber is visible above the second surface of the backing in the bonded portion of the fiber. Inspection from more than one angle may be necessary to visualize the entirety of the surface area of the fiber. The term "loft-retaining bond" when referring to the bonding of fibrous materials means a bonded fibrous material comprises a loft that is at least 80% of the loft exhibited by the material prior to, or in the absence of, the bonding process. The loft of a fibrous material as used herein is the ratio of the total volume occupied by the web (including fibers as well as interstitial spaces of the material that are not occupied by fibers) to the volume occupied by the material of the fibers alone. If only a portion of a fibrous web has the second surface of the backing bonded thereto, the retained loft can be easily ascertained by comparing the loft of the fibrous web in the bonded area to that of the web in an unbonded area. It may be convenient in some circumstances to compare the loft of the bonded web to that of a sample of the same web before being bonded, for example, if the entirety of fibrous web has the second surface of the backing bonded thereto. In some of these embodiments, the joining comprises impinging heated gaseous fluid (e.g., ambient air, dehumidified air, nitrogen, an inert gas, or other gas mixture) onto a first surface of the fibrous web carrier while it is moving; impinging heated fluid onto the second surface of the backing while the continuous web is moving, wherein the second surface is opposite the fibrous layer, loop, or upstanding posts the backing; and contacting the first surface of the fibrous web with the second surface of the backing so that the first surface of the fibrous web is melt-bonded (e.g., surface-bonded or bonded with a loft-retaining bond) to the second surface of the backing. Impinging heated gaseous fluid onto the first surface of the fibrous web and impinging heated gaseous fluid on the second surface of the backing may be carried out sequentially or simultaneously. Further methods and apparatus for joining a continuous web to a fibrous carrier web using heated gaseous fluid may be found in U.S. Pat. Appl. Pub. Nos. 2011/0151171 (Biegler et al.) and 2011/0147475 (Biegler et al.).

In some embodiments wherein the spread mechanical fastening web is joined to a carrier, one or more zones of the carrier may comprise one or more elastically extensible materials extending in at least one direction when a force is applied and returning to approximately their original dimension after the force is removed. However, in some embodiments, at least the portion of the carrier joined to the multiple strands of the backing or loop material is not stretchable. In some embodiments, the portion of carrier joined to the multiple strands will have up to a 10 (in some embodiments, up to 9, 8, 7, 6, or 5) percent elongation in the CD. In some embodiments, the carrier may be extensible but nonelastic. In other words, the carrier may have an elongation of at least 5, 10, 15, 20, 25, 30, 40, or 50 percent but substantially no recovery from the elongation (e.g., up to 10 or 5 percent recovery). Suitable extensible carriers may include nonwovens (e.g., spunbond, spunbond meltblown spunbond, or carded nonwovens). In some embodiments, the nonwoven may be a high elongation carded nonwoven (e.g., HEC). In some embodiments, the carrier is not pleated.

In some embodiments wherein the spread mechanical fastening web is joined to a carrier, the carrier is provided with a layer of adhesive. In some of these embodiments, the spread mechanical fastening web is bonded to the carrier with the adhesive to form a laminate, and the adhesive is exposed between the multiple strands in the laminate.

In some embodiments, the method according to the present disclosure includes cutting the spread mechanical fastening web in the CD to provide a spread mechanical fastening patch. Such cutting can be carried out, for example, after the spread mechanical fastening web is laminated to a carrier, and the patch can be considered a fastening laminate.

The fastening laminates made by the methods disclosed herein are useful, for example, in absorbent articles. Absorbent articles may have at least a front waist region, a rear waist region, and a longitudinal center line bisecting the front waist region and the rear waist region, wherein at least one of the front waist region or the rear waist region comprises the fastening laminate disclosed herein. The fastening laminate may be in the form of a fastening tab or landing zone that is bonded to at least one of the front waist region or the rear waist region. A fastening tab may extend outwardly from at least one of the left longitudinal edge or the right longitudinal edge of the absorbent article. In other embodiments, the fastening laminate may be an integral ear portion of the absorbent article. The carrier at the user's end of a fastening tab may exceed the extension of the spread mechanical fastening patch thereby providing a fingerlift. When the spread mechanical fastening patch is used in a fastening tab, exposed adhesive that may be present in some embodiments between the multiple strands of the spread mechanical fastening patch may be useful for "anti-flagging" or for maintaining the disposable absorbent article in a rolled up state after use. Also when the spread mechanical fastening patch is used as a landing zone or fastening tab, exposed adhesive that may be present in some embodiments between the multiple strands of the spread mechanical fastening patch may be useful to provide a combination of mechanical and adhesive fastening. The fastening laminate made by the methods disclosed herein may also be useful, for example, for disposable articles such as sanitary napkins.

The mechanical fasteners and laminates made according to the present disclosure may also be useful in many other fastening applications, for example, assembly of automotive parts or any other application in which releasable attachment may be desirable.

Some Embodiments of the Disclosure

In a first embodiment, the present disclosure provides a method of making a mechanical fastener, the method comprising:

providing a slit web having mechanical fastening elements and a length in a machine direction, wherein the slit web includes a plurality of laterally separated interrupted slits that are interrupted by intact bridging regions of the web, wherein the intact bridging regions divide the interrupted slits into a series of spaced slit portions aligned in the machine direction, and wherein for at least some adjacent interrupted slits, the spaced slit portions are staggered in a cross-machine direction; and spreading the slit web in the cross-machine direction by directing the slit web over at least a first roller having first multiple protrusions around its peripheral surface, wherein the first multiple protrusions are positioned such that adjacent protrusions push through consecutive slit portions of a first one, two, or three of the interrupted slits to form a spread mechanical fastening web, wherein the spread mechanical fastening web comprises multiple strands of the slit web attached to each other at least at some of the intact bridging regions and separated from each other between at least some of the intact bridging regions. The first multiple protrusions may form a single row around the peripheral surface of the first roller to push through the consecutive slit portions of a first one of the interrupted slits, may be in the form of multiple pairs of protrusions forming two identical rows around the peripheral surface of the first roller to push through the consecutive slit portions of a first two of the interrupted slits, or may be in the form of a combination of these wherein the single row is centered between and offset from the multiple pairs of protrusions forming two identical rows to push through the consecutive slit portions of a first three of the interrupted slits.

In a second embodiment, the present disclosure provides the method of the first embodiment, wherein the first multiple protrusions are centered on the peripheral surface of the first roller.

In a third embodiment, the present disclosure provides the method of the first or second embodiment, further comprising directing the slit web over at least one second roller having multiple paired of protrusions around its peripheral surface, wherein the multiple paired protrusions are positioned such that adjacent pairs push through consecutive slit portions of second and third of the interrupted slits, wherein the second and third of the interrupted slits are on opposite sides of the first one, two, or three of the interrupted slits.

In a fourth embodiment, the present disclosure provides the method of any one of the first to third embodiments, wherein the second and third of the interrupted slits are adjacent the first one, two, or three of the interrupted slits.

In the fifth embodiments, the present disclosure provides the method of any one of the first to fourth embodiments, further comprising directing the slit web over a series of second rollers, each having multiple paired protrusions around its peripheral surface, wherein for each second roller, the multiple paired protrusions are positioned such that adjacent pairs push through consecutive slit portions of an opposing pair of the interrupted slits, wherein the opposing pair of the interrupted slits are on opposite sides of the first of the interrupted slits, and wherein for each consecutive roller in the series of second rollers, the paired protrusions and the opposing pair of the interrupted slits are spaced progressively further apart.

In a sixth embodiment, the present disclosure provides the method of any one of the third to fifth embodiments, wherein the multiple paired protrusions are centered on the peripheral surface of the second roller.

In seventh embodiment, the present disclosure provides the method of any one of the first to fourth embodiments, further comprising directing the slit web over a series of third rollers, each having multiple groups of protrusions around its peripheral surface, wherein for each third roller, the multiple groups of protrusions are positioned such that adjacent groups push through consecutive slit portions of a series of the interrupted slits, and wherein for each consecutive roller in the series of third rollers, the number of protrusions in each of the multiple groups of protrusions increases as the number of interrupted slits in the series of the interrupted slits increases.

In an eighth embodiment, the present disclosure provides the method of the seventh embodiment, wherein the multiple groups of protrusions are centered on the peripheral surface of each third roller.

In a ninth embodiment, the present disclosure provides the method of any one of the fifth to eighth embodiments, wherein the slit web is directed over the first roller such that the mechanical fastening elements face away from the first roller, and wherein the slit web is directed over each consecutive roller in the series of rollers such that the mechanical fastening elements alternate facing toward the roller and then away from the roller.

In a tenth embodiment, the present disclosure provides the method of any one of the first to ninth embodiments, wherein the protrusions are pins. The pins may be symmetrical or not.

In an eleventh embodiment, the present disclosure provides the method of any one of the first to ninth embodiments, wherein the protrusions are ribs. The ribs may be symmetrical or not.

In a twelfth embodiment, the present disclosure provides the method of any one of the first to eleventh embodiments, wherein tension applied in the machine direction causes the protrusions to push through the slit portions.

In a thirteenth embodiment, the present disclosure provides the method of any one of the first to twelfth embodiments, wherein directing the slit web over the first roller, second roller, and/or series of second or third rollers comprises directing the slit web through a nip comprising the first, second, or third roller and a mating roller for the first, second, or third roller, wherein the mating roller comprises depressions that align with the multiple protrusions, multiple paired protrusions, or multiple groups of protrusions.

In a fourteenth embodiment, the present disclosure provides the method of any one of the first to thirteenth embodiments, wherein vacuum applied on the slit web causes the protrusions to push through the slit portions.

In a fifteenth embodiment, the present disclosure provides the method of any one of the first to thirteenth embodiments, wherein air blown onto the slit web causes the protrusions to push through the slit portions.

In a sixteenth embodiment, the present disclosure provides the method of the fifteenth embodiment, wherein the air is heated.

In a seventeenth embodiment, the present disclosure provides the method of any one of the first to sixteenth embodiments, further comprising heating the spread mechanical fastening web, for example, to anneal the spread mechanical fastening web.

In a eighteenth embodiment, the present disclosure provides the method of the seventeenth embodiment, wherein the first roller, the second roller, and/or at least one roller in the series of second or third rollers is heated.

In a nineteenth embodiment, the present disclosure provides the method of the seventeenth or eighteenth embodiment, wherein heating comprises directing the spread mechanical fastening web onto a rotating heated cylinder.

In a twentieth embodiment, the present disclosure provides the method of the seventeenth embodiment, wherein heating the spread mechanical fastening web comprises using non-contact heating.

In a twenty-first embodiment, the present disclosure provides the method of any one of the first to twentieth embodiments, further comprising directing the spread mechanical fastening web onto a high-friction roller.

In a twenty-second embodiment, the present disclosure provides the method of the twenty-first embodiment, wherein the high-friction roller is heated.

In a twenty-third embodiment, the present disclosure provides the method of the twenty-first embodiment, wherein the high-friction roller is chilled.

In a twenty-fourth embodiment, the present disclosure provides the method of any one of the first to twenty-third embodiments, further comprising directing the spread mechanical fastening web onto a rotating chilled cylinder.

In a twenty-fifth embodiment, the present disclosure provides the method of any one of the first to twenty-fourth embodiments, further comprising laminating the spread mechanical fastening web to a carrier.

In a twenty-sixth embodiment, the present disclosure provides the method of the twenty-fifth embodiment, wherein the carrier is a nonwoven web.

In a twenty-seventh embodiment, the present disclosure provides the method of the twenty-fifth or twenty-sixth embodiment, wherein the carrier is provided with a layer of an adhesive.

In a twenty-eighth embodiment, the present disclosure provides the method of the twenty-seventh embodiment, wherein the spread mechanical fastening web is bonded to the carrier with the adhesive to form a laminate, and wherein the adhesive is exposed between the multiple strands in the laminate.

In a twenty-ninth embodiment, the present disclosure provides the method of any one of the first to twenty-eighth embodiments, wherein the mechanical fastening elements are male fastening elements comprising upstanding posts having bases attached to the slit web. The male fastening elements may also comprise caps distal from the slit web.

In a thirtieth embodiment, the present disclosure provides the method of the twenty-ninth embodiment, further comprising providing a thermoplastic backing having multiple rows of the upstanding posts, wherein providing the slit web comprises slitting through the thermoplastic backing between at least some pairs of adjacent rows of the upstanding posts.

In a thirty-first embodiment, the present disclosure provides the method of the twenty-ninth or thirtieth embodiment, wherein the caps have loop-engaging overhangs extending beyond the upstanding posts at a non-zero angle to the direction of the interrupted slits.

In a thirty-second embodiment, the present disclosure provides the method of any one of the twenty-ninth to thirty-first embodiments, wherein the width dimension of each of the multiple strands is wider than at least the bases of the upstanding posts.

In a thirty-third embodiment, the present disclosure provides the method of any one of the first to thirty-second embodiments, wherein there is no macroscopic stretch-induced molecular orientation in the slit backing in the cross-direction.

In a thirty-fourth embodiment, the present disclosure provides the method of any one of the first to thirty-third embodiments, wherein the multiple strands of the slit web attached to each other at least at some of the intact bridging regions form an angle of less than 90 degrees.

In a thirty-fifth embodiment, the present disclosure provides an apparatus for spreading a slit web, the apparatus comprising multiple rollers configured to handle a web in a continuous process, the multiple rollers comprising:
a first roller having first multiple protrusions around its peripheral surface, and
at least one subsequent roller having multiple sets of at least two protrusions around its peripheral surface. The first multiple protrusions may form a single row around the peripheral surface of the first roller, may be in the form of multiple pairs of protrusions forming two identical rows around the peripheral surface of the first roller, or may be in the form of a combination of these wherein the single row is centered between and offset from the multiple pairs of protrusions forming two identical rows. The at least one subsequent roller may be a second roller having multiple paired protrusions around its peripheral surface.

In a thirty-sixth embodiment, the present disclosure provides the apparatus of the thirty-fifth embodiment, wherein the at least one subsequent roller is a second roller included in a series of second rollers, each having multiple paired protrusions around its peripheral surface, wherein for each consecutive roller in the series of second rollers, the paired protrusions are spaced progressively further apart.

In a thirty-seventh embodiment, the present disclosure provides the apparatus of the thirty-fifth embodiment, wherein the at least one subsequent roller is a third roller included in a series of third rollers, each having multiple groups of protrusions around its peripheral surface, wherein for each consecutive roller in the series of third rollers, the number of protrusions in each of the multiple groups of protrusions increases.

In a thirty-eighth embodiment, the present disclosure provides the apparatus of any one of the thirty-fifth to thirty-seventh embodiments, wherein the first multiple protrusions are centered on the peripheral surface of the first roller, and/or wherein the multiple sets of at least two protrusions are centered on the peripheral surface of each subsequent roller.

In a thirty-ninth embodiment, the present disclosure provides the apparatus of any one of the thirty-fifth to thirty-eighth embodiments, wherein the protrusions are pins.

In a fortieth embodiment, the present disclosure provides the apparatus of any one of the thirty-fifth to thirty-eighth embodiments, wherein the protrusions are ribs.

In a forty-first embodiment, the present disclosure provides the apparatus of any one of the thirty-fifth to fortieth embodiments, the first roller and/or the at least one subsequent roller is capable of being heated.

In a forty-second embodiment, the present disclosure provides the apparatus of any one of the thirty-fifth to forty-first embodiments, further comprising a rotating heated cylinder.

In forty-third embodiment, the present disclosure provides the apparatus of any one of the thirty-fifth to forty-second embodiments, further comprising a high-friction roller.

In forty-fourth embodiment, the present disclosure provides the apparatus of any one of the thirty-fifth to forty-third embodiments, further comprising a rotating chilled cylinder.

This disclosure is not limited to the above-described embodiments but is to be controlled by the limitations set forth in the following claims and any equivalents thereof. This disclosure may be suitably practiced in the absence of any element not specifically disclosed herein.

What is claimed is:

1. A method of making a mechanical fastener, the method comprising:
providing a slit web having mechanical fastening elements and a length in a machine direction, wherein the slit web includes a plurality of laterally separated interrupted slits that are interrupted by intact bridging regions of the web, wherein the intact bridging regions divide the interrupted slits into a series of spaced slit portions aligned in the machine direction, and wherein for at least some adjacent interrupted slits, the spaced slit portions are staggered in a cross-machine direction; and
spreading the slit web in the cross-machine direction by directing the slit web over at least a first roller having first multiple protrusions around its peripheral surface, wherein the first multiple protrusions are positioned such that adjacent protrusions push through consecutive slit portions of a first one, two, or three of the interrupted slits to form a spread mechanical fastening web, wherein the spread mechanical fastening web comprises multiple strands of the slit web attached to each other at least at some of the intact bridging regions and separated from each other between at least some of the intact bridging regions.

2. The method of claim 1, wherein the first multiple protrusions form a single row around the peripheral surface of the first roller, and wherein the adjacent protrusions push through the consecutive slit portions of one of the interrupted slits.

3. The method of claim 1, further comprising directing the slit web over at least one second roller having multiple paired protrusions around its peripheral surface, wherein the multiple paired protrusions are positioned such that adjacent pairs push through consecutive slit portions of second and third of the interrupted slits, wherein the second and third of the interrupted slits are on opposite sides of the first one, two, or three of the interrupted slits.

4. The method of claim 1, further comprising directing the slit web over a series of second rollers, each having multiple paired protrusions around its peripheral surface, wherein for each second roller, the multiple paired protrusions are positioned such that adjacent pairs push through consecutive slit portions of an opposing pair of the interrupted slits, wherein the opposing pair of the interrupted slits are on opposite sides of the first one, two, or three of the interrupted slits, and wherein for each consecutive roller in the series of second rollers, the paired protrusions and the opposing pair of the interrupted slits are spaced progressively further apart.

5. The method of claim 4, wherein the multiple paired protrusions are centered on the peripheral surface of each second roller.

6. The method of claim 4, wherein at least one second roller in the series of second rollers is heated.

7. The method of claim 1, further comprising directing the slit web over a series of third rollers, each having multiple groups of protrusions around its peripheral surface, wherein for each third roller, the multiple groups of protrusions are positioned such that adjacent groups push through consecutive slit portions of a series of the interrupted slits, and wherein for each consecutive roller in the series of third rollers, the number of protrusions in each of the multiple groups of protrusions increases as the number of interrupted slits in the series of the interrupted slits increases.

8. The method of claim 7, wherein at least one third roller in the series of third rollers is heated.

9. The method of claim 1, wherein tension applied in the machine direction causes the protrusions to push through the slit portions.

10. The method of claim 1, further comprising at least one of heating the spread mechanical fastening web or directing the spread mechanical fastening web onto a high-friction roller.

11. The method of claim 10, wherein heating comprises directing the spread mechanical fastening web onto a rotating heated cylinder.

12. The method of claim 1, further comprising laminating the spread mechanical fastening web to a carrier.

13. The method of claim 12, wherein the carrier is provided with a layer of an adhesive, wherein the spread mechanical fastening web is bonded to the carrier with the adhesive to form a laminate, and wherein the adhesive is exposed between the multiple strands in the laminate.

14. The method of claim 12, wherein the carrier is a nonwoven web.

15. The method of claim 1, wherein the mechanical fastening elements are male fastening elements comprising upstanding posts having bases attached to the slit web.

16. The method of claim 1, wherein the slit web has loops.

* * * * *